(12) United States Patent
Yasuda et al.

(10) Patent No.: US 6,506,908 B2
(45) Date of Patent: Jan. 14, 2003

(54) PROCESS FOR PREPARING 3-HYDROXYMETHYL-4-(ARYL OR HETEROCYCLIC)-CYCLOPENTANONES

(75) Inventors: Nobuyoshi Yasuda, Mountainside, NJ (US); Michael Palucki, Hillsborough, NJ (US); Joann M. Um, Franklin Lakes, NJ (US); David Alan Conlon, Plainsboro, NJ (US); Barry M. Trost, Los Altos, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/838,989

(22) Filed: Apr. 20, 2001

(65) Prior Publication Data

US 2002/0016492 A1 Feb. 7, 2002

Related U.S. Application Data

(60) Provisional application No. 60/199,088, filed on Apr. 21, 2000.

(51) Int. Cl.$^7$ .......................... C07D 333/02; C07C 69/74
(52) U.S. Cl. ........................................ 549/78; 568/715
(58) Field of Search ............................ 549/78; 568/715

(56) References Cited

U.S. PATENT DOCUMENTS

| | | | |
|---|---|---|---|
| 4,073,799 A | 2/1978 | Kondo et al. | ................ 549/421 |
| 5,468,469 A | 11/1995 | Aszalos et al. | .............. 514/150 |

FOREIGN PATENT DOCUMENTS

| | | |
|---|---|---|
| WO | WO 00/76972 | 12/2000 |

OTHER PUBLICATIONS

T. J. Schall, "Biology of the Rantes/sis Cytokine Family", Cytokine, vol. 3, No. 3, May 1991, pp. 165–183.
P. M. Murphy, "The Molecular Biology of Leukocyte Chemoattractant Receptors", Annual Review of Immunology, vol. 12, 1994, pp. 593–633.
H. Deng et al., "Identification of a major co–receptor for primary isolates of HIV–1", Nature, vol. 381, Jun. 1996, pp. 661–666.
R. Horuk, "Molecular properties of the chemokine receptor family", Trends Pharm. Science, vol. 15, 1994, pp. 159–165.
A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.
K. Neote et al., "Molecular Cloning, Functional Expression, and Signaling Characteristics of a C–C Chemokine Receptor", Cell, vol. 72, Feb. 1993, pp. 415–425.
C. Combadiere et al., "Cloning and Functional Expression of a Human Eosinophil CC Chemokine Receptor", J. Biol. Chem. vol. 270, No. 27, Jul. 1995, pp. 16491–16494.

C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.
M. Samson et al., "Molecular Cloning and Functional Expression of a New Human CC–Chemokine Receptor Gene", Biochemistry, vol. 35, 1996, pp. 3362–3367.
A. Chaudhuri et al., "Expression of the Duffy Antigen in K562 Cells,", J. Biol. Chem., vol. 269, No. 11, Mar. 1994, pp. 7835–7838.
J.J. Gomez–Reino et al., "Association of Rheumatoid Arthritis with a Functional Chemokine Receptor, CCR5", Arthritis & Rheumatism, vol. 42, No. 5, May 1999, pp. 989–992.
H. Kita et al., "Chemokines Active on Eosinophils: Potential Roles in Allergic Inflammation", J. Exp. Med., vol. 183, Jun. 1996, pp. 2421–2426.
D. Smith et al., "Blocking of HIV–1 Infectivity by a Soluble, Secreted Form of the CD4 Antigen", Science, vol. 238, 1987, pp. 1704–1707.
J. A. Levy, "Infection by Human Immunodeficiency Virus—CD is not Enough", N. Eng. J. Med., vol. 335, No. 20, Nov. 1996), pp. 1528–1530.
T. Dragic et al., "HIV–1 entry into CD4+ cells is mediated by the chemokine receptor CC–CKR5", Nature, vol. 381, Jun. 1996, pp. 667–673.
L. Wu et al., "CD4–induced interaction of primary HIV–1 gp120 glycoproteins with the chemokine receptor CCR–5", Nature, vol. 384, Nov. 1996, pp. 179–183.
A. Trkola et al., "CD4–dependent, antibody–sensitive interactions between HIV–1 and its co–receptor CCR–5", Nature, vol. 384, Nov. 1996, pp. 184–187.
M. Samson et al., "Resistance to HIV–1 infection in caucasian individuals bearing mutant alleles of the CCR–5 chemokine receptor gene", Nature, vol. 382, Aug. 1996, pp. 722–725.
C. M. Hill et al., "Natural resistance to HIV?", Nature, vol. 382, Aug. 1996, pp. 668–669.

(List continued on next page.)

Primary Examiner—Zinna Northington Davis
(74) Attorney, Agent, or Firm—Kenneth R. Walton; Melvin Winokur

(57) ABSTRACT

Processes are disclosed for preparing 3-hydroxymethylcyclopentanone compounds, which are useful as intermediates in the preparation of HIV chemokine CCR-5 receptor antagonists. A process is described in which the compounds are prepared by opening the cyclopropyl ring of a (1-alkoxycarbonyl-2-oxo)-trans-bicyclo[3.1.0]hexane compound by addition of a nucleophile to the cyclopropyl ring, and then decarboxylating the resulting 2-alkoxycarbonyl-3-(Nu-methyl)-cyclopentanone (Nu=the added nucleophilic group) via base solvolysis. Also described is a process for preparing the bicyclo[3.1.0]hexane precursors by the catalyzed cyclopropanation of a suitable alpha-diazo-beta-ketoester. The preparation of the alpha-diazo-beta-ketoesters and precursors thereto are also disclosed.

31 Claims, No Drawings

OTHER PUBLICATIONS

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

Callant et al., "The Synthesis of Functionalized cis–Bicyclo [3.3.0] Octanes", Tetrahedron, vol. 37, 1981, pp. 2079–2084.

S. Tanimori et al., "A New Nucleophilic Ring Opening of an Activated Cyclopropane and Formal Synthesis of (+)–Carbovir", Biosci. Biotech. Biochem., vol. 59, No. 11, 1995, pp. 2091–2093.

S. Tanimori et al., "A Concise Enantioselective Pathway to Carbocyclic Nucleoside: Asymmetric Synthesis of Carbocyclic Moiety of Carbovir", Synthetic Commun., vol. 27, No. 14, 1997, pp. 2371–2378.

B. Trost et al., "Asymmetric Molybdenum–Catalyzed Alkylations", J. Amer. Chem. Soc., vol. 120, 1998, pp. 1104–1105.

B. Trost et al., "Regio– and Enantioselective Molybdenum–Catalyzed Alkylations of Polyenyl Esters", J. Amer. Chem. Soc., vol. 121, 1999, pp. 10416–10417.

F. Glorios et al., "Enantioselective Molybdenum–Catalyzed Allylic Alkylation Using Chiral Bisoxazoline Ligands", Organic Letters, vol. 1, 1999, pp. 141–144.

A. K. Ghosh et al., "$C_2$Symmetric chiral bis(oxazoline)–metal complexes in catalytic asymmetric synthesis", Tetrahedron: Asymmetry 9, 1998, pp. 1–45.

PROCESS FOR PREPARING 3-HYDROXYMETHYL-4-(ARYL OR HETEROCYCLIC)-CYCLOPENTANONES

This patent application claims the benefit of U.S. provisional patent application Ser. No. 60/199,088, filed Apr. 21, 2000.

FIELD OF THE INVENTION

The present invention relates to processes for preparing 3-hydroxymethylcyclopentanone compounds. The cyclopentanones can be employed as intermediates in the production of piperidinylmethyl-cyclopentyl derivatives which are modulators of chemokine receptor activity. In particular, the piperidinylmethyl-cyclopentyl derivatives are HIV chemokine CCR-5 receptor inhibitors and are useful in the treatment of infection by HIV and in the treatment of AIDS and ARC.

References are made throughout this application to various published documents in order to more fully describe the state of the art to which this invention pertains. The disclosures of these references are hereby incorporated by reference in their entireties.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C—C ($\beta$), depending on whether the first two cysteines are separated by a single amino acid (C-X-C) or are adjacent (C—C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1 $\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least seven human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al.,*J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al.,*J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al.,*J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al.,*Arthritis & Rheumatism*, 42, 989–992 (1999)). A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., Science, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (Nature, 382, 722–725 (1996)). Absence of CCR-5 appears to confer substantial protection from HIV-1 infection (Nature, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (Nature Medicine, 2(11), 1240–1243 (1996)). Nevertheless, drugs targeting chemokine receptors may not be unduly compromised by the genetic diversity of HIV-1 (Zhang, et al., Nature, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. A compound from Takeda, TAK-779, reportedly is a nonpeptidal CCR5 antagonist with anti-HIV-1 activity (Baba, et al., Proc. Natl Acad. Sci., USA, 96, 5698–5703 (1999)). As noted above, the inhibitors of HIV-1 replication present in supernatants of CD8+ T cells have been characterized as the β-chemokines RANTES, MIP-1α and MIP-1β.

N-Cyclopentyl compounds such as those depicted in the following Formula (A) are HIV CCR5 antagonists useful for preventing or treating infection by HIV and useful for preventing or treating AIDS or ARC:

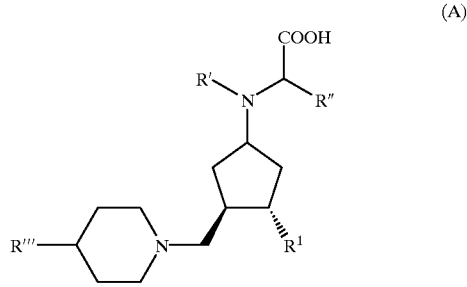

(A)

wherein $R^1$ is as defined and described below (see, e.g., the Summary of the Invention);

R' is hydrogen, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)-$C_{3-8}$ cycloalkyl, naphthyl, biphenyl, or heterocycle, which is unsubstituted or substituted with one or more of substituents independently selected from halo, trifluoromethyl, hydroxy, $C_{1-3}$ alkyl, —O—$C_{1-3}$ alkyl, —$CO_2R''$, —NR''R$^v$, and —CONRUR$^v$;

R" independently has the same definition as R';

or alternatively R' and R" are joined together to form a 3–8 membered saturated azacycloalkyl ring which may be unsubstituted or substituted with one or more substituents independently selected from halo, trifluoromethyl, hydroxy, $C_{1-3}$ alkyl, —O—$C_{1-3}$ alkyl, —$CO_2R''$, —NR''R$^v$, and —CONR''R$^v$;

R''' is A—R$^s$;

A is selected from ($C_{0-4}$ alkyl)-G-($C_{0-4}$ alkyl), ($C_{0-6}$ alkyl)-$C_{3-8}$ cycloalkyl-($C_{0-6}$ alkyl), $C_{2-10}$ alkenyl, and $C_{2-10}$ alkynyl, where the alkyl is unsubstituted or substituted with one or more substituents where the substituents are independently selected from halo, hydroxy, —O—$C_{1-3}$ alkyl, and trifluoromethyl; and G is selected from a single bond, —O—, —$SO_2$—, —NR$^v$—, —NR$^v$—$SO_2$—, —$SO_2$—NR$^v$—, —S—, and —SO—;

R" is independently selected from hydrogen, $C_{1-6}$ alkyl, $C_{5-6}$ cycloalkyl, benzyl or phenyl, which is unsubstituted or substituted with one or more substituents where the substituents are independently selected from: halo, $C_{1-3}$ alkyl, $C_{1-3}$ alkoxy and trifluoromethyl, R$^v$ is independently selected from hydrogen, $C_{1-6}$ alkyl, benzyl, phenyl, and $C_{1-6}$ alkyl-$C_{3-6}$ cycloalkyl, which is unsubstituted or substituted with one or more substituents where the substituents are independently selected from: halo, $C_{1-3}$ alkyl, $C_{1-3}$ alkoxy and trifluoromethyl; and R$^s$ is selected from hydrogen, $C_{3-8}$ cycloalkyl, phenyl, naphthyl, biphenyl, and heterocycle, which is unsubstituted or substituted with one or more substituents each of which is independently selected from halo; cyano; hydroxy; $C_{1-6}$ alkyl, which is unsubstituted or substituted with one or more of R$^t$ where R$^t$ is independently selected from halo, cyano, hydroxy, $C_{1-6}$ alkoxy, —$CO_2H$, —$CO_2(C_{1-6}$ alkyl), trifluoromethyl, and —NR"R$^v$; —O—$C_{1-6}$ alkyl, which is unsubstituted or substituted with one or more of R$^t$; —$CF_3$; —$CHF_2$; —$CH_2F$; —$NO_2$; $C_{0-6}$ alkyl-phenyl or $C_{0-6}$ alkyl-heterocycle, which is unsubstituted or substituted with one or more substituents where the substituents are independently selected from halo, hydroxy, $C_{1-6}$ alkyl, —O—$C_{1-6}$ alkyl, —$CF_3$, —$OCF_3$, —$NO_2$, —CN, —$SO_2$—$C_{1-6}$ alkyl, —$CO_2R''$, —NR"R$^v$, —CONR"R$^v$, —$SO_2$—NR"R$^v$, and —NR"—$SO_2$-R$^v$; —$CO_2R''$; tetrazolyl; —NR"R$^v$; —NR"—COR$^v$; —NR"—$CO_2R''$; —CO—NR"R$^v$; —OCO—NR"R$^v$; —NR"CO—NR"R$^v$; —S(O)$_{0-2}$—R"; —S(O)$_2$—NR"R$^v$; —NR"S(O)$_2$—R$^v$; and —NR"S(O)$_2$—NR"R$^v$;

or a pharmaceutically acceptable salt thereof.

Further description of the N-cyclopentyl compounds of Formula (A) and of other cyclopentyl compounds that are CCR5 antagonists is provided in WO 00/76972.

Methods for preparing compounds of Formula (A) involve a key cyclopentanone intermediate, which itself can be prepared via routes involving a {3+2} cycloaddition with a chiral auxiliary, as shown in Schemes A and B below. Unfortunately, these routes result in a racemic mixture (i.e., a5 and b3 in Schemes A and B respectively), which require tedious separation by, for example, chiral chromatography to obtain the desired hydroxymethylcyclopentanone isomer (i.e., a8 in Schemes A and B). There is a need for a method of preparing the desired cyclopentanone intermediate which avoids the production of its diastereomer(s) or which provides for the efficient separation of the desired intermediate from its diastereomer(s).

Scheme A

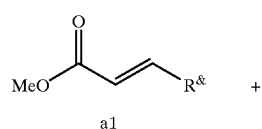

a1

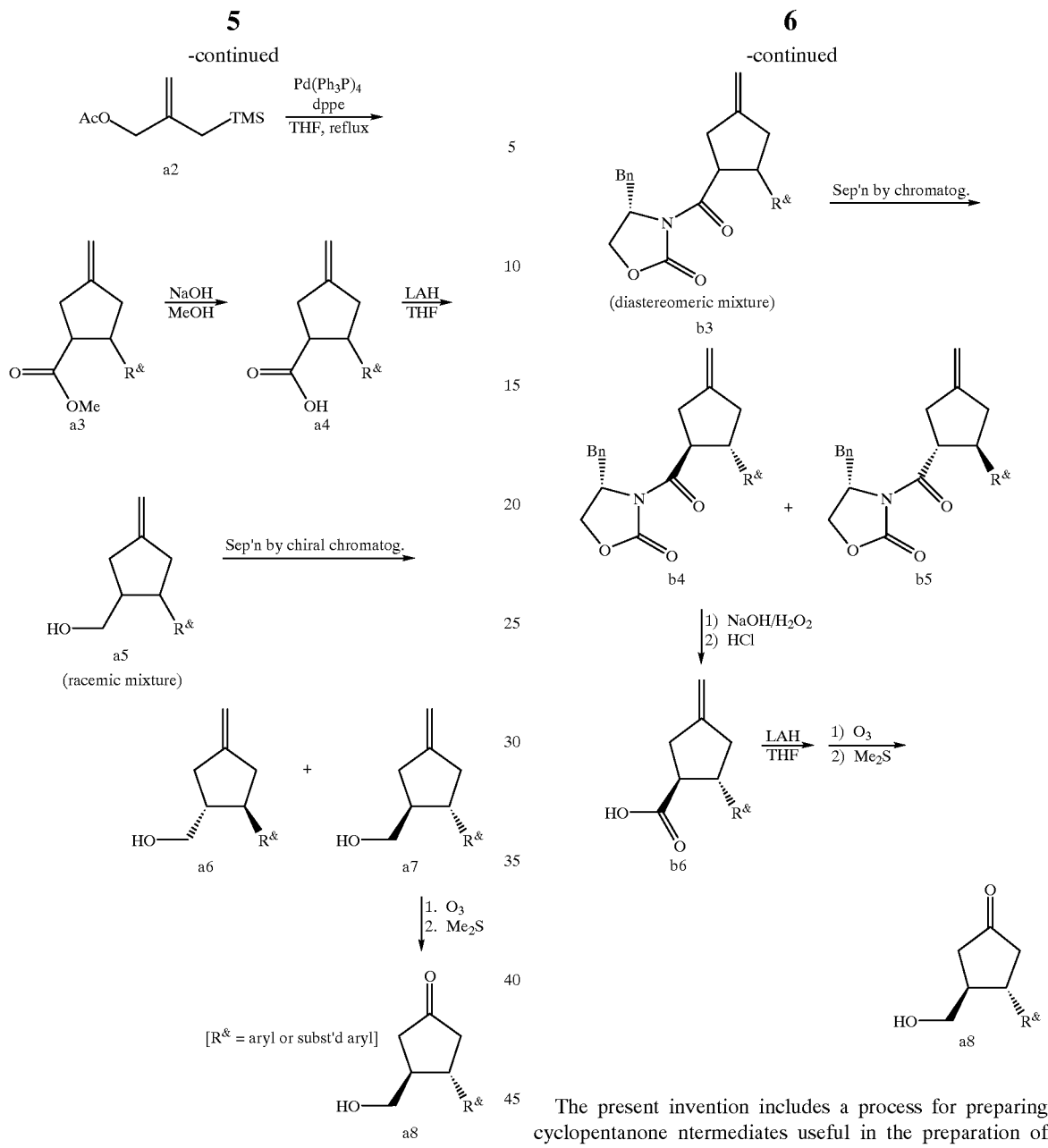

The present invention includes a process for preparing cyclopentanone ntermediates useful in the preparation of compounds of Formula (A), wherein the process includes opening the cyclopropyl ring of a (1-alkoxycarbonyl-2-oxo)-trans-bicyclo[3.1.0]hexane via nucleophilic addition, followed by decarboxylation via base solvolysis to obtain the desired cyclopentanone intermediate. An embodiment of the present invention relates to the metal-catalyzed intramolecular cyclopropanation of a diazo compound to form the bicyclo[3.1.0]hexane compound employed in the nucleophilic addition. The present invention also includes the alkylation of a vinyl carbonate with a malonate salt in the presence of a molybdenum catalyst complex prepared from molybdenum hexacarbonyl and a chiral ligand, wherein the alkylated product is a precursor to the diazo compound of the preceding sentence. As will become apparent from the detailed description set forth below, the present invention provides a route for producing the desired cyclopentanone intermediate which does not involve the {3+2} cycloaddition chemistry depicted above in Schemes A and B, which does not form a diastereomer of the desired intermediate, and which permits the easy and efficient recovery and isolation of the intermediate.

References of interest with respect to the present invention are as follows:

U.S. Pat. No. 4,073,799 (Kondo et al., 1978) discloses a process for producing 3-formylcyclopentanone derivatives which involves, inter alia, forming certain α-diazo-β-dicarbonyl compounds by reaction of the corresponding β-dicarbonyl compounds with an azide under basic conditions, treating the formed diazo compounds with a catalyst or photoirradiation so as to form bicyclo[3.1.0] hexane-2-one derivatives, and reacting the bicyclo derivatives with a mercaptan in the presence of base to open the cyclopropyl ring via addition of SH⁻.

Callant et al., *Tetrahedron* 1981, 37: 2079–2084, discloses the preparation of 2-methoxycarbonyltricyclo[3.3.1.0$^{2,8}$] octan-3-one by the intramolecular cyclopropanation of methyl 2-diazo-3-oxo-4-(2-cyclopentenyl) butyrate in the presence of copper(II) acetylacetonate. The reference also discloses the preparation of the diazo compound by reaction of methyl 3-oxo-4-(2-cyclopentenyl) butyrate in acetonitrile with p-toluenesulfonyl azide and triethylamine.

Tanomori et al., *Biosci. Biotech. Biochem.* 1995, 59: 2091–2093, discloses the reaction of 1-methoxycarbonyl-2-oxo-bicyclo[3.1.0]hexane with potassium acetate and acetic acid in dimethylsulfoxide at 90° C. (4 hours) to obtain 2-methoxycarbonyl-3-acetyl-cyclopentanone. The reference further discloses a formal total synthesis of (+)-carbovir by conversion of the cyclopentanone.

Tanomori et al., *Synthetic Commun.* 1997, 27: 2371–2378, discloses the internal cyclopropanation of an ester of 2-diazo-3-oxo-6-heptenoic acid in dichloromethane solution at −15° C. using rhodium(II) acetate as the catalyst. The reference also discloses the preparation of the diazo compound from the 3-oxo-6-heptenoic acid ester using p-toluenesulfonyl azide and triethylamine in acetonitrile.

Trost et al., *J. Am. Chem. Soc.* 1998, 120: 1104–1105, discloses the molybdenum-catalyzed asymmetric alkylation of methyl 3-phenylprop-2-en-1-ol carbonate with sodium dimethyl malonate using $(C_2H_5CN)_3Mo(CO)_3$ and a 1,2-bis-(2-pyridylcarbonylamino)cyclohexane chiral ligand.

Trost et al., *J. Am. Chem. Soc.* 1999, 121: 10416–10417, discloses regio- and enantio- selective molybdenum-catalyzed alkylation of certain polyenyl esters using $(C_2H_5CN)_3Mo(CO)_3$ and a 1,2-bis-(2-pyridylcarbonylamino)-cyclohexane chiral ligand.

Glorius et al., *Organic Letters* 1999, 1: 141–144, discloses the synthesis of a series of chiral $C_2$-symmetric bis-oxazolines with trans-1,2-diamninocyclohexane backbones and their use in enantioselective molybdenum-catalyzed alkylations of certain 1- and 3-monosubstituted allylic substrates.

SUMMARY OF THE INVENTION

The present invention is directed to an improved process for preparing cyclopentanone derivatives useful as intermediates in the production of piperidinylmethyl-cyclopentyl derivatives which are modulators of chemokine receptor activity. More specifically, the present invention is a process for preparing a hydroxymethylcyclopentanone compound of Formula (XII):

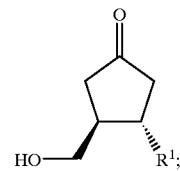

(XII)

which comprises (Z4) reacting a mixture comprising a trans-bicyclo[3.1.0] hexane compound of Formula (X):

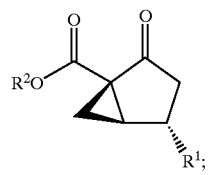

(X)

and a nucleophilic agent in solvent at a temperature in a range of from about 20 to about 200° C. to open the fused cyclopropyl ring of Compound X by addition of the nucleophile; and (Z5) contacting the reaction mixture of step Z4 with a base to form Compound XII;

wherein $R^1$ is phenyl, substituted phenyl, heterocycle, or substituted heterocycle, wherein each of the substituents on substituted phenyl or substituted heterocycle is independently selected from:

(a) halo, (b) trifluoromethyl, (c) hydroxy, (d) $C_1$–$C_3$ alkyl, (e) $C_1$–$C_3$ alkoxy, (f) —$CO_2R^a$, (g) —$NR^aR^b$, and (h) —$CONR^aR^b$;

$R^2$ is $C_1$–$C_4$ alkyl, $C_1$–$C_4$ haloalkyl, or $C_2$–$C_6$ alkoxyalkyl;

each $R^a$ is independently hydrogen, $C_1$–$C_6$ alkyl, $C_1$–$C_6$ haloalkyl, $C_2$–$C_8$ alkoxyalkyl, $C_5$–$C_6$ cycloalkyl, benzyl, phenyl, substituted $C_5$–$C_6$ cycloalkyl, substituted benzyl or substituted phenyl, wherein each of the substituents on substituted $C_5$–$C_6$ cycloalkyl, substituted benzyl or substituted phenyl is independently selected from halo, nitro, $C_1$–$C_3$ alkyl, $C_1$–$C_3$ alkoxy and trifluoromethyl; and each $R^b$ is independently hydrogen, $C_1$–$C_6$ alkyl, $C_1$–$C_6$ haloalkyl, $C_2$–$C_8$ alkoxyalkyl, benzyl, phenyl, —$C_1$–$C_6$ alkyl-$C_3$–$C_6$ cycloalkyl, substituted benzyl, substituted phenyl, or substituted —$C_1$–$C_6$ alkyl-$C_3$–$C_6$ cycloalkyl, wherein each of the substituents on substituted benzyl, substituted phenyl, or substituted —$C_1$–$C_6$ alkyl-$C_3$–$C_6$ cycloalkyl is independently selected from halo, nitro, $C_1$–$C_3$ alkyl, $C_1$–$C_3$ alkoxy and trifluoromethyl.

Embodiments of the present invention include the process as set forth above further comprising the preparation of Compound X from a diazo precursor and optionally the preparation of the diazo precursor by reaction of a beta-ketoester with a sulfonyl azide. These and other embodiments, aspects and features of the present invention are either further described in or will be apparent from the ensuing description, examples and appended claims.

DETAILED DESCRIPTION OF THE INVENTION

The present invention is concerned with processes for preparing 3-hydroxymethylcyclopentanone compounds of Formula (XII), which are useful as intermediates in the preparation of HIV chemokine CCR-5 receptor antagonists. Scheme C as follows (the variables being defined elsewhere in the specification) illustrates the process steps involved in various aspects and embodiments of the present invention:

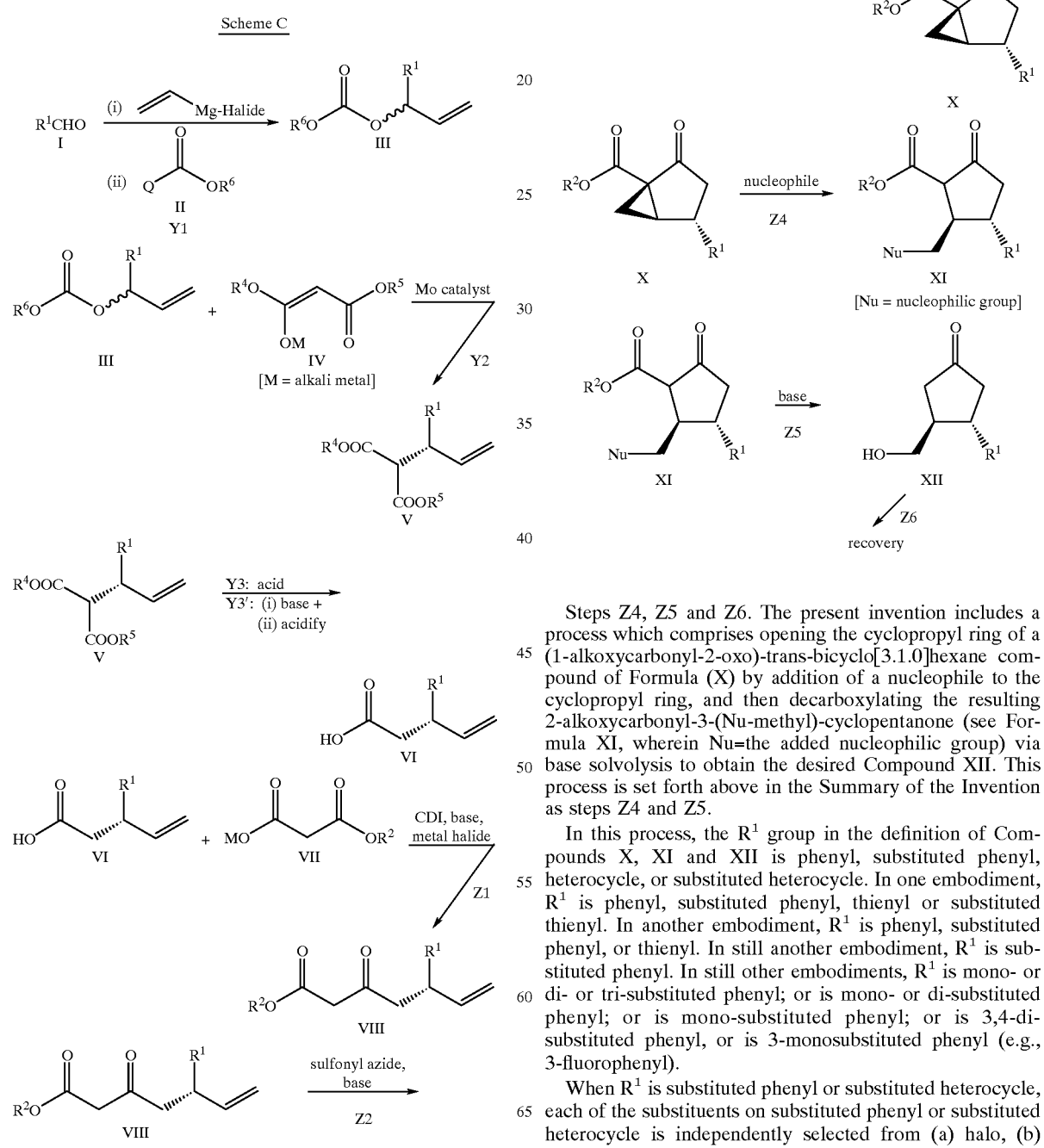

Steps Z4, Z5 and Z6. The present invention includes a process which comprises opening the cyclopropyl ring of a (1-alkoxycarbonyl-2-oxo)-trans-bicyclo[3.1.0]hexane compound of Formula (X) by addition of a nucleophile to the cyclopropyl ring, and then decarboxylating the resulting 2-alkoxycarbonyl-3-(Nu-methyl)-cyclopentanone (see Formula XI, wherein Nu=the added nucleophilic group) via base solvolysis to obtain the desired Compound XII. This process is set forth above in the Summary of the Invention as steps Z4 and Z5.

In this process, the $R^1$ group in the definition of Compounds X, XI and XII is phenyl, substituted phenyl, heterocycle, or substituted heterocycle. In one embodiment, $R^1$ is phenyl, substituted phenyl, thienyl or substituted thienyl. In another embodiment, $R^1$ is phenyl, substituted phenyl, or thienyl. In still another embodiment, $R^1$ is substituted phenyl. In still other embodiments, $R^1$ is mono- or di- or tri-substituted phenyl; or is mono- or di-substituted phenyl; or is mono-substituted phenyl; or is 3,4-di-substituted phenyl, or is 3-monosubstituted phenyl (e.g., 3-fluorophenyl).

When $R^1$ is substituted phenyl or substituted heterocycle, each of the substituents on substituted phenyl or substituted heterocycle is independently selected from (a) halo, (b) trifluoromethyl, (c) hydroxy, (d) $C_1$–$C_3$ alkyl, (e) $C_1$–$C_3$ alkoxy, (f) —CO$_2$R$^a$, (g) —NR$^a$R$^b$, and (h) —CONR$^a$R$^b$. In one embodiment, each of the substituents on substituted phenyl or substituted heterocycle is independently selected from (a) halo, (b) trifluoromethyl, (c) hydroxy, (d) C$_1$–C$_3$ alkyl, and (e) C$_1$–C$_3$ alkoxy. In another embodiment, each of the substituents on substituted phenyl or substituted heterocycle is independently selected from fluoro and chloro. In other embodiments, each of the substituents is selected from fluoro, chloro, trifluoromethyl, hydroxy, methyl, ethyl, methoxy, and ethoxy; or is selected from fluoro, chloro, trifluoromethyl, methyl, and methoxy; or is fluoro.

When one or more of the substituents on substituted phenyl or substituted heterocycle is (f) —CO$_2$R$^a$, (g) —NR$^a$R$^b$, and (h) —CONR$^a$R$^b$, each R$^a$ is independently hydrogen, C$_1$–C$_6$ alkyl, C$_1$–C$_6$ haloalkyl, C$_2$–C$_8$ alkoxyalkyl, C$_5$–C$_6$ cycloalkyl, benzyl, phenyl, substituted C$_5$–C$_6$ cycloalkyl, substituted benzyl, or substituted phenyl, wherein each of the substituents on substituted C$_5$–C$_6$ cycloalkyl, substituted benzyl or substituted phenyl is independently selected from halo, C$_1$–C$_3$ alkyl, C$_1$–C$_3$ alkoxy and trifluoromethyl; and each R$^b$ is independently hydrogen, C$_1$–C$_6$ alkyl, C$_1$–C$_6$ haloalkyl, C$_2$–C$_8$ alkoxyalkyl, benzyl, phenyl, C$_1$–C$_6$ alkyl-C$_3$–C$_6$ cycloalkyl, substituted benzyl, substituted phenyl, or substituted C$_1$–C$_6$ alkyl-C$_3$–C$_6$ cycloalkyl, wherein each of the substituents on substituted benzyl, substituted phenyl, or substituted C$_1$–C$_6$ alkyl-C$_3$–C$_6$ cycloalkyl is independently selected from halo, C$_1$–C$_3$ alkyl, C$_1$–C$_3$ alkoxy and trifluoromethyl.

In one embodiment, each R$^a$ is independently hydrogen, C$_1$–C$_3$ alkyl, C$_1$–C$_3$ haloalkyl, C$_2$–C$_4$ alkoxyalkyl, C$_5$–C$_6$ cycloalkyl, benzyl, phenyl, substituted C$_5$–C$_6$ cycloalkyl, substituted benzyl or substituted phenyl, wherein each of the substituents on substituted C$_5$–C$_6$ cycloalkyl, substituted benzyl or substituted phenyl is independently selected from halo, C$_1$–C$_3$ alkyl, C$_1$–C$_3$ alkoxy and trifluoromethyl. In another embodiment, each R$^a$ is independently hydrogen, C$_1$–C$_3$ alkyl, C$_1$–C$_3$ fluoroalkyl, C$_2$–C$_4$ alkoxyalkyl, C$_5$–C$_6$ cycloalkyl, benzyl, or phenyl. In other embodiments, each R$^a$ is independently hydrogen, C$_1$–C$_3$ alkyl, (CH$_2$)$_{0-2}$CF$_3$, (CH$_2$)$_{1-2}$OCH$_3$, C$_5$–C$_6$ cycloalkyl, benzyl, or phenyl; or is hydrogen, methyl, ethyl, CF$_3$, or CH$_2$OCH$_3$; or is hydrogen.

In one embodiment, each R$^b$ is independently hydrogen, C$_1$–C$_3$ alkyl, C$_1$–C$_3$ haloalkyl, C$_2$–C$_4$ alkoxyalkyl, benzyl, phenyl, -C$_1$–C$_3$ alkyl-C$_3$–C$_6$ cycloalkyl, substituted benzyl, substituted phenyl, or substituted -C$_1$–C$_3$ alkyl-C$_3$–C$_6$ cycloalkyl, wherein each of the substituents on substituted benzyl, substituted phenyl, or substituted -C$_1$–C$_3$ alkyl-C$_3$–C$_6$ cycloalkyl is independently selected from halo, C$_1$–C$_3$ alkyl, C$_1$–C$_3$ alkoxy and trifluoromethyl. In another embodiment, each R$^b$ is independently hydrogen, C$_1$–C$_3$ alkyl, C$_1$–C$_3$ fluoroalkyl, C$_2$–C$_4$ alkoxyalkyl, benzyl, phenyl, or -C$_1$–C$_3$ alkyl-C$_3$–C$_6$ cycloalkyl. In other embodiments, each R$^b$ is independently hydrogen, C$_1$–C$_3$ alkyl, (CH$_2$)$_{0-2}$CF$_3$, (CH$_2$)$_{1-2}$OCH$_3$, benzyl, phenyl, or —C$_1$–C$_3$ alkyl-C$_3$–C$_6$ cycloalkyl; or is hydrogen, methyl, ethyl, CF$_3$, or CH$_2$OCH$_3$; or is hydrogen.

In this process, the R$^2$ group in the definition of Compounds X and XI is C$_1$–C$_4$ alkyl, C$_1$–C$_4$ haloalkyl, or C$_2$–C$_6$ alkoxyalkyl. In one embodiment, R$^2$ is C$_1$–C$_4$ alkyl, C$_1$–C$_4$ fluoroalkyl, or C$_2$–C$_6$ alkoxyalkyl. In another embodiment, R$^2$ is C$_1$–C$_3$ alkyl, C$_1$–C$_3$ fluoroalkyl, or C$_2$–C$_4$ alkoxyalkyl. In still another embodiment, R$^2$ is C$_1$–C$_3$ alkyl, (CH$_2$)$_{0-2}$CF$_3$, or (CH$_2$)$_{1-2}$OCH$_3$. In other embodiments, R$^2$ is methyl, ethyl, CF$_3$, or methoxymethyl; or is methyl or CF$_3$; or is methyl or ethyl; or is methyl.

In step Z4 the nucleophilic agent can be any agent capable of adding a nucleophilic group to Compound X under the reaction conditions employed in step Z4. Suitable nucleophiles include, but are not limited to, those selected from the group consisting of alkali metal salts of C$_1$–C$_6$ alkylcarboxylic acids, alkaline earth metal salts of C$_1$–C$_6$ alkylcarboxylic acids, C$_1$–C$_6$ thioalcohols, C$_1$–C$_6$ alkylamines, N-(C$_1$–C$_4$ alkyl)-C$_1$–C$_6$ alkylamines, C$_5$–C$_7$ cycloalkylamines, C$_5$–C$_7$ azacycloalkanes, alkali metal C$_1$–C$_6$ alkoxides, alkali metal amides, and alkali metal cyanides. Exemplary nucleophiles include NaOAc, KOAc, Mg(OAc)$_2$, sodium proprionate, methanethiol, ethanethiol, methylamine, ethylamine, n-propylamine, cyclopentylamine, piperidine, piperazine, NaOEt, NaOPr, NaNH$_2$, KNH$_2$, NaCN, and KCN. In one embodiment, the nucleophile is an alkali metal salt of a C$_1$–C$_6$ alkylcarboxylic acid. In an aspect of the preceding embodiment, the nucleophile is an alkali metal acetate (e.g., NaOAc).

The nucleophilic agent can be employed in step Z4 in any proportion with respect to Compound X which will result in at least some cleavage of the cyclopropyl ring in X. For example, the amount of nucleophilic agent employed in Z4 can be at least about 0.5 equivalent per mole equivalent of Compound X. The amount of nucleophile is typically in the range of from about 0.7 to about 20 mole equivalents per equivalent of Compound X, and is more typically in the range of from about 1 to about 20 mole equivalents per equivalent of Compound X. In one embodiment, the amount of nucleophile is from about 1 to about 10 (e.g., from about 1.05 to about 5) mole equivalents per mole equivalent of Compound X. In another embodiment, the amount of nucleophilic agent is in the range of from about 1.1 to about 4 (e.g., from about 1.1 to about 2) mole equivalents per mole equivalent of Compound X.

Suitable solvents in step Z4 include, but are not limited to, carboxylic acids, amides and esters of carboxylic acids, aliphatic and cyclic ethers and diethers, nitrites, amines, and sulfoxides. Exemplary solvents include acetic acid, propionic acid, butyric acid, valeric acid, DMF, DMA, ethyl ether, methy t-butyl ether, propyl ether, THF, dioxane, acetonitrile, propionitrile, valeronitrile, NMP, DMPU and dimethylsulfoxide. In one embodiment, the solvent is selected from the group consisting of C$_1$–C$_6$ alkylcarboxylic acids, dialkylformamides wherein each alkyl is independently a C$_1$–C$_4$ alkyl, dialkylacetamides wherein each alkyl is independently a C$_1$–C$_4$ alkyl, dialkyl ethers wherein each alkyl is independently a C$_1$–C$_6$ alkyl, C$_4$–C$_6$ cyclic ethers and diethers, C$_2$–C$_6$ aliphatic nitriles, NMP, and dimethylsulfoxide. In another embodiment, the solvent is selected from the group consisting of acetic acid, DMF, DMA, and NMP.

Step Z4 is suitably conducted at a temperature in a range of from about 20 to about 200° C. (e.g., from about 40 to about 200° C.), and is typically conducted at a temperature in a range of from about 50 to about 130° C. In one embodiment, the temperature is in a range of from about 70 to about 120° C. In another embodiment, the temperature is in the range of from about 90 to about 120° C. (e.g., from about 95 to about 115° C.).

The reactants can be added to the reaction vessel (also referred to herein as the reaction "pot") in Z4 concurrently, either together or separately, or they can be added sequentially in either order. The solvent can be added before, during, or after addition of Compound X or the nucleophile or both Compound X and the nucleophile. In one embodiment, Compound X pre-mixed with the solvent is charged to the reaction vessel followed by addition of the nucleophile, which is charged all at once at the start or added in portions or incrementally during the reaction.

The ring-opened adduct formed in step Z4 (i.e., Compound XI) can be isolated using conventional techniques, but isolation of the product is typically not necessary. Step Z5 can proceed in the same reaction pot without any work-up.

In step Z5, the base can be any organic or inorganic base which can decarboxylate the ring-opened adduct formed in step Z4 and form thereby Compound XII. Suitable bases include, but are not limited to, bases selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl)ammonium hydroxides, and tri-($C_1$–$C_4$ alkyl)amines. Exemplary bases include hydroxides, carbonates, and oxides of lithium, sodium and potassium; methoxides, ethoxides, and n- and iso-propoxides of lithium, sodium, and potassium; tetramethyl- and tetraethyl-ammonium hydroxide; triethylamine; and diisopropylethylamine. In one embodiment, the base is selected from the group consisting of alkali metal hydroxides. In an aspect of the preceding embodiment, the base is NaOH or KOH.

The base can be employed in step Z5 in any proportion with respect to Compound X which will result in the formation of at least some of Compound XII. The amount of base employed in step Z5 of the process can suitably be at least about 0.01 equivalent per mole equivalent of Compound X, and is typically in the range of from about 0.01 to about 20 mole equivalents per equivalent of Compound X. In one embodiment, the amount of base is from about 0.1 to about 10 (e.g., from about 0.5 to about 5) equivalents per equivalent of Compound X. In another embodiment, the amount of base is in the range of from about 1 to about 5 equivalents per equivalent of Compound X.

Step Z5 is suitably conducted at a temperature in the range of from about 20 to about 110° C., and is typically conducted at a temperature in the range of from about 50 to about 90° C. In one embodiment, the temperature is in the range of from about 60 to about 80° C. (e.g., from about 65 to about 75° C.).

As noted above, steps Z4 and Z5 are typically conducted in the same pot, wherein the base is added to the Z4 reaction vessel to initiate step Z5. Of course, step Z5 can be conducted in a separate reaction vessel in the event the ring-opened adduct of Compound X is recovered. The recovered adduct and base can be added to a reaction vessel concurrently, either together in a mixture or separately, or they can be added sequentially in either order. If a solvent is used, the solvent can be added before, during, or after addition of the base or the adduct or both the base and adduct. In one embodiment, the adduct XI pre-mixed with solvent is charged to the reaction vessel, followed by addition of base, which can be added all at once at the start of the solvolysis or can be added periodically in portions or added incrementally during the reaction. Suitable solvents include the solvents described above as suitable for step Z4.

Yields of Compound XII from Compound X via steps Z4 and Z5 of at least about 75% can be achieved when using stoichiometric or higher amounts of nucleophile and base with respect to Compound X. Yields of 85% or more, or even 90% or more (e.g., from about 90 to about 99%), can typically be achieved.

A preferred aspect of the present invention is a process for preparing

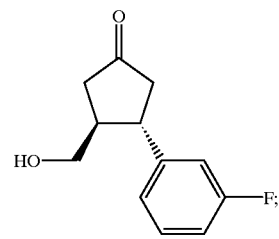

12 which comprises:

(Z4) reacting a mixture comprising

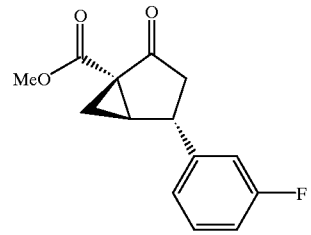

10 and a nucleophilic agent in solvent (e.g., sodium acetate in acetic acid) at a temperature in a range of from about 20 to about 200° C. (preferably from about 50 to about 130° C.) to open the fused cyclopropyl ring of 10;

(Z5) contacting the reaction mixture of step Z4 with a base (e.g., an alkali metal hydroxide at a temperature in the range of from about 20 to about 100° C.) to form 12.

As set forth more fully below in the description of step Z3, Compound X can be prepared by the catalyzed cyclopropanation of the appropriate alpha-diazo-beta-ketoester (see Compound IX below). The cyclopropanation reaction typically results in a mixture containing trans and cis bicycloheptanes; i.e., compounds of Formula (X) and (X') respectively:

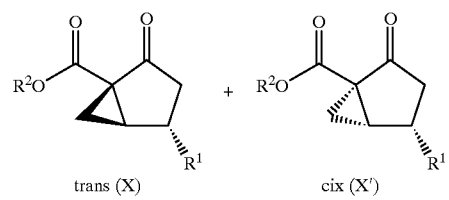

trans (X)              cix (X')

It has been unexpectedly discovered that the cyclopropyl ring of the cis isomer (Compound X') does not open under the reaction conditions employed in step Z4. Base solvolysis of the Z4 product mixture in step Z5 will provide the desired Compound XII via decarboxylation along with a cis carboxylic acid of Formula XIII:

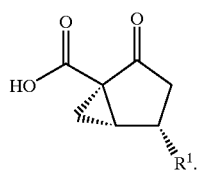

(XIII)

Thus, an embodiment the present invention is a process for preparing a hydroxymethylcyclopentanone compound of Formula (XII):

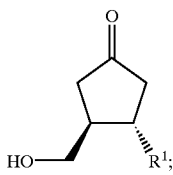

(XII)

which comprises:

(Z4) reacting a mixture comprising a trans-bicyclo[3.1.0] hexane compound of Formula (X) and a cis-bicyclo[3.1.0] hexane compound of Formula (X') and a nucleophilic agent in solvent at a temperature in a range of from about 20 to about 200° C. to open the fused cyclopropyl ring of Compound X by addition of the nucleophile;

(Z5) contacting the reaction mixture of step Z4 with a base to form a mixture of Compound XII and a compound of Formula (XIII); and (Z6) recovering Compound XII from the mixture; wherein $R^1$ and $R^2$ are as defined above. All embodiments and features defined and described above for steps Z4 and Z5 (e.g., reaction temperatures and times, choice of solvents, and so forth) define analogous embodiments and features in the process that includes Z6.

Compound XII can be conveniently and easily recovered from the mixture of Compounds XII and XIII by a simple extraction with an organic solvent under aqueous basic conditions.

Step Z3. In another embodiment of the invention, the process for preparing 3-hydroxymethylcyclopentanone compounds of Formula (XII) further comprises, in addition to steps Z4 and Z5, and optionally Z6, as set forth above, a step Z3, which comprises contacting a diazo compound of Formula (IX):

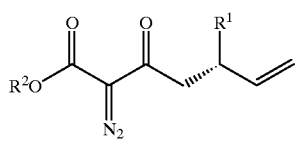

(IX)

with a transition metal catalyst in solvent to form Compound X.

In step Z3 the catalyst can be an organic or inorganic salt of a transition metal of Groups Ib, IIb, IIIb, IVb, Vb, VIb, VIb, or VIII (equivalent to Groups 3 to 12 in the new IUPAC notation) of the Periodic Table of the Elements (78th edition of the *Handbook of Chemistry and Physics*, CRC Press (1997)). The catalyst can be selected from nitrates, thiocyanates, halides, carboxylates, phosphates, thiophospates, sulfates, and borates of transition metals, including, but not limited to, iron, cobalt, nickel, copper, chromium, manganese, molybdenum, tungsten, ruthenium, rhodium, palladium, platinum, zirconium, cadmium, lead, silver, mercury, and antimony.

In one embodiment, the catalyst is an organic or inorganic salt of rhodium, cobalt, copper, ruthenium, or zirconium. Suitable cobalt and ruthenium catalysts include those described in Charette and Lebel, "Cyclopropanation and C—H Insertion with Metals Other Than Cu and Rh", Chapter 16.3 in *Comprehensive Asymmetric Catalysis II*, E. N. Jacobsen, A. Pfaltz, and H. Yamamoto (editors), Springer (1999), pp. 581–603, and references cited therein.

An aspect of the preceding embodiment is a catalyst which is a salt of rhodium or copper. Suitable rhodium catalysts include, but are not limited to, rhodium salts of $C_1$–$C_{10}$ alkylcarboxylic acids, such as $Rh_2(acetate)_4$, $Rh_2(caproate)_4$, and $Rh_2(octanoate)_4$.

Also suitable are rhodium(II)carboxylates of formula $Rh_2(OCOR^*)_4$ wherein R* is a chiral group selected from N-benzenesulfonyl-(S)-prolinyl, 4-tert-butyl-N-benzenesulfonyl-(S)-prolinyl, 4-dodecyl-N-benzenesulfonyl-(S)-prolinyl, N-phthaloyl-(S)-phenylalaninyl, N-phthaloyl-(S)-alaninyl, N-phthaloyl-(S)-valinyl, and N-phthaloyl-(S)-tert-leucinyl. The foregoing chiral catalysts may be depicted as follows:

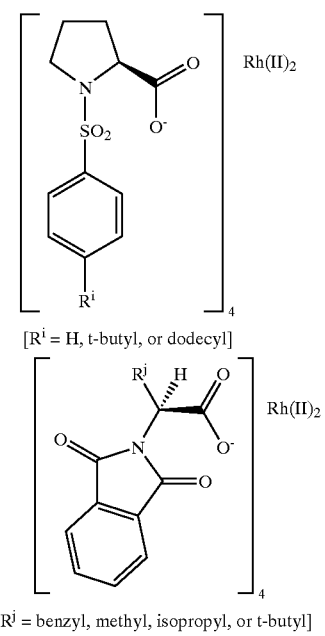

[$R^i$ = H, t-butyl, or dodecyl]

[$R^j$ = benzyl, methyl, isopropyl, or t-butyl]

Other suitable rhodium salts include chiral rhodium(II) carboxamidates, including the following:

$Rh_2(5S-mepy)_4$:

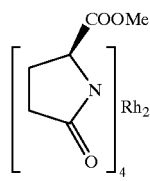

Rh₂(5R-mepy)₄:
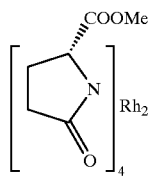

Rh₂(5S-nepy)₄:
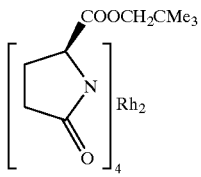

Rh₂(5S-odpy)₄:
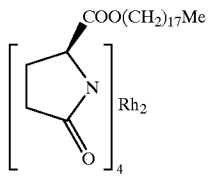

Rh₂(5S-dmap)₄:
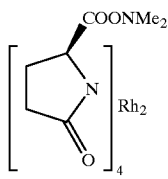

Rh₂(4S-meox)₄:
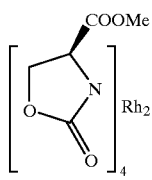

Rh₂(4S-threox)₄:
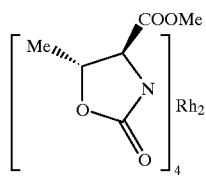

Rh₂(4S-bnox)₄:
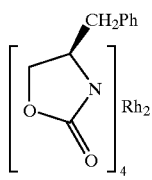

Rh₂(4S-ipox)₄:
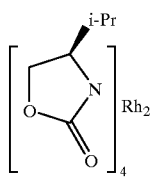

Rh₂(4S-phox)₄:
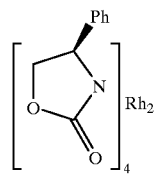

Rh₂(4S-mppim)₄:
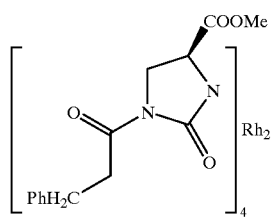

Rh₂(4S-macim)₄:
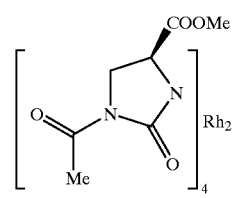

Further description of the foregoing chiral rhodium catalysts and of other chiral rhodium catalysts suitable for use in step Z3 is in Lydon and McKervey, "Cyclopropanation and C-H Insertion with Rh", Chapter 16.2 in *Comprehensive Asymmetric Catalysis II*, E. N. Jacobsen, A. Pfaltz, and H. Yamamoto (editors), Springer (1999), pp. 539–580, and references cited therein.

Copper catalysts are preferred over rhodium catalysts, because for the same or similar reaction conditions they typically have better selectivity for the trans product X over the cis byproduct X'. Suitable copper catalysts include, but are not limited to, CuO, $Cu_2O$, copper salts of $C_1$–$C_{10}$ alkylcarboxylic acids (e.g., Cu(I)OAc and $Cu(OAc)_2$), the triflate salts (e.g., CuOTf and $Cu(OTf)_2$), and hexafluorophosphate salts (e.g., $[(CH_3CN)_4Cu]PF_6$). Another suitable copper catalyst is a mixture of CuCl and AgOTf.

A preferred catalyst class is a catalyst selected from the group consisting of $Cu(OTf)_2$, $[(CH_3CN)_4Cu]PF_6$, and CuCl+AgOTf.

In one embodiment, the catalyst comprises a copper(I) catalyst represented by the formula:

$$[L_pCu(I)]Q^-;$$

wherein each L is a ligand independently selected from $C_2$–$C_6$ olefins (e.g., ethylene, propylene, isobutene, or n-butene), aliphatic $C_2$–$C_6$ nitriles (e.g., acetonitrile), aliphatic $C_1$–$C_4$ alkyl alcohols (e.g., methanol, ethanol, and isopropanol), aliphatic $C_2$–$C_6$ ethers and di-ethers (e.g., ethyl ether and dimethoxyethane), and $C_4$–$C_6$ cyclic ethers and di-ethers (e.g., THF and dioxane); p is an integer in the range from 0 to 4; and $Q^-$ is a counterion. Suitable counterions include, but are not limited to, non-nucleophilic groups such as $PF_6^-$, $SbF_6^-$, halide ($F^-$, $Cl^-$, $Br^-$, or $I^-$), $ClO_4^-$, and $OTf^-$. These catalysts are commercially available (e.g., from Aldrich Chemical Company and Strem Chemicals), or can be prepared by conventional methods such as reacting the copper counterion salt with the ligand (e.g., heating CuClO$_4$ with acetonitrile to form (MeCN)$_4$Cu$^+$ ClO$_4^-$) or reacting the copper(I) oxide with the ligand in the presence of the counterion (e.g., reacting copper(I) oxide with acetonitrile in the presence of perchloric acid).

In one aspect of the preceding embodiment, the copper(I) catalyst comprises a catalyst of formula [L$_p$Cu(I)]Q$^-$, as defined in the preceding paragraph, complexed with a chiral ligand. Suitable chiral ligands include, but are not limited to, bis-oxazolines represented by one of the following formulas:

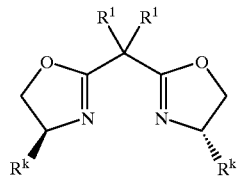

R$^k$ = C$_{1-6}$ alkyl (e.g., CMe$_3$ or CHMe$_2$), phenyl, or benzyl
R$^1$ = H or Me

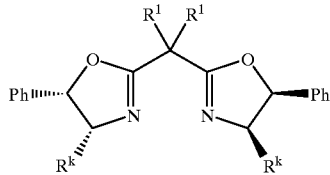

R$^k$ = C$_{1-6}$ alkyl (e.g., CMe$_3$ or CHMe$_2$), phenyl, or benzyl
R$^1$ = H or Me Exemplary bis-oxazoline ligands are 2,2'-methylenebis[(4S)-4-t-Bu-2-oxazoline], 2,2'-methylenebis[(4S)-4-Ph-2-oxazoline], R-(−)-2,2'-isopropylenebis(4-Ph-2-oxazoline), S-(+)-2,2'-isopropylenebis(4-Ph-2-oxazoline), R-methylenebis-dihydro-indeno-oxazole, and S-methylenebis-dihydro-indeno-oxazole. Further description of the above and other suitable bis-oxazoline ligands and their preparation is provided in Ghosh et al., *Tetrahedron: Asymmetry* 1998, 9: 1–45, and references cited therein.

In another aspect of the preceding embodiment, the copper(I) catalyst is a catalyst comprising [(CH$_3$CN)$_4$Cu] PF$_6$, optionally complexed with a chiral ligand as described in the preceding paragraph. The catalyst is commercially available (e.g., Aldrich), or can be prepared by heating a mixture of the acetonitrile with CuPF$_6$ in a suitable solvent (e.g., THF) or by heating a mixture of copper(I) oxide and acetonitrile in the presence of hexafluorophosphoric acid. A detailed preparation of the catalyst is provided in Kubas, *Inorg. Synth.* 1979, XIX: 90–92. If desired, the resulting [(CH$_3$CN)$_4$Cu]PF$_6$ can then be complexed with a ligand by heating a mixture of the ligand and catalyst in a suitable solvent (e.g., THF).

In another embodiment, the copper catalyst is a semicorrin catalyst of formula:

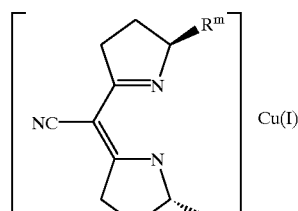

R$^m$ = CMe$_2$OH, COOMe, or CH$_2$OSiMe$_2$-t-Bu.

Further description of the chiral copper catalysts described above and of other chiral copper catalysts suitable for use in step Z3 is in Pfaltz, "Cyclopropanation and C-H Insertion with Cu", Chapter 16.1 in *Comprehensive Asymmetric Catalysis II*, E. N. Jacobsen, A. Pfaltz, and H. Yamamoto (editors), Springer (1999), pp. 513–538, and references cited therein.

Any amount of catalyst can be employed which results in the formation of at least some of Compound X. The amount of catalyst employed in step Z3 is suitably in the range of from about 0.001 to about 30 (e.g., from about 0.01 to about 10) mole percent transition metal (e.g., Rh or Cu), and is typically from about 0.1 to about 30 (e.g., from about 0.3 to about 30) mole percent transition metal, based on the total moles of transition metal and Compound IX. In one embodiment, the catalyst is a copper catalyst and the amount of copper catalyst is in the range of from about 0.01 to about 10 mole percent (e.g., from about 0.3 to about 10 mole percent). In an aspect of the preceding embodiment, the copper catalyst is present in an amount in the range of from about 0.3 to about 3 mole percent. In another aspect of the preceding embodiment, the copper catalyst is present in an amount in the range of from about 1 to about 3 mole percent.

As noted above, step Z3 typically produces a cis-bicyclo[3.1.0]hexane compound of Formula X' in addition to the trans compound of Formula X. Compound IX is typically washed with water or treated with silica prior to use in step Z3. It has been found that the use of purified IX can reduce the catalyst load required to achieve high conversion and can also improve the trans/cis product ratio.

Suitable solvents for step Z3 include, but are not limited to, C$_3$–C$_{20}$ linear and branched alkanes, C$_1$–C$_{12}$ linear and branched halogenated alkanes, C$_5$–C$_{10}$ cycloalkanes, C$_6$–C$_{14}$ aromatic hydrocarbons, dialkyl ethers wherein each alkyl is independently a C$_1$–C$_{10}$ alkyl, C$_4$–C$_8$ dialkoxyalkanes, C$_4$–C$_8$ cyclic ethers and diethers, C$_6$–C$_8$ aromatic ethers, C$_2$–C$_{10}$ dialkyl ketones wherein each alkyl is independently C$_1$–C$_8$ alkyl, C$_1$–C$_6$ alkyl esters of C$_1$–C$_6$ alkylcarboxylic acids, primary C$_1$–C$_{10}$ alkyl alcohols, secondary C$_3$–C$_{10}$ alkyl alcohols, tertiary C$_4$–C$_{10}$ alkyl alcohols, primary amides of C$_1$–C$_6$ alkylcarboxylic acids, N—C$_1$–C$_6$ alkyl secondary amides or N,N-di-C$_1$–C$_6$ alkyl tertiary amides of C$_1$–C$_6$ alkylcarboxylic acids, C$_2$–C$_6$ aliphatic nitriles, and C$_7$–C$_{10}$ aromatic nitriles. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, acetone, methyl ethyl ketone (MEK), methyl acetate, ethyl acetate, ethanol, n- and isopropanol, tert-butyl alcohol, dimethylformamide (DMF), acetonitrile, propionitrile, benzonitrile, and p-tolunitrile.

In one embodiment, the solvent is selected from the group consisting of C$_3$–C$_{12}$ linear and branched alkanes, C$_2$–C$_6$ linear and branched halogenated alkanes, $C_5$–$C_7$ cycloalkanes, $C_6$–$C_{10}$ aromatic hydrocarbons, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, $C_2$–$C_6$ dialkyl ketones wherein each alkyl is independently a $C_1$–$C_5$ alkyl, $C_1$–$C_4$ alkyl acetates, N,N-di-($C_1$–$C_4$) alkyl tertiary amides of $C_1$–$C_6$ alkylcarboxylic acids, $C_1$–$C_6$ alkyl alcohols, $C_2$–$C_6$ aliphatic nitriles, and $C_7$–$C_{10}$ aromatic nitriles. In another embodiment, the solvent is selected from the group consisting of $C_2$–$C_6$ linear and branched halogenated alkanes, dialkyl ethers wherein each alkyl is independently a $C_1$–$C_6$ alkyl, $C_4$–$C_8$ dialkoxyalkanes, and $C_4$–$C_6$ cyclic ethers and diethers. In an aspect of the preceding embodiment, the solvent is selected from the group consisting of DCE, TCE, toluene, and THF. In another, preferred aspect of the preceding embodiment, the solvent is DCE.

Step Z3 is suitably conducted at a temperature in a range of from about 15 to about 100° C. (e.g., from about 25 to about 100° C.), and is typically conducted at a temperature in a range of from about 25 to about 90° C. In one embodiment, the temperature is in a range of from about 70 to about 100° C. (e.g., from about 75 to about 95° C.). In an aspect of the preceding embodiment, the temperature is in a range of from about 75 to about 100° C. (e.g., from about 75 to about 90° C.).

Compounds of Formula (IX) present a potential safety hazard, because they can be unstable, possibly explosive. Accordingly, Compound IX is normally not employed in an isolated form, but is instead handled in solution form at low temperatures (i.e., less than about 25° C.) and is used as soon as practicable after being prepared. Typically, the catalyst mixed with a portion of solvent is added to the reaction vessel first and brought to reaction temperature, followed by the slow addition of a cold solution (i.e., a temperature of from about 1 to about 25° C.) of Compound IX prepared with another portion of solvent. It is preferred to add the solution of Compound IX to the catalyst solution sufficiently slowly over the entire reaction period such that there will be minimal to no accumulation of Compound IX throughout the cyclopropanation.

When the reaction is complete or the desired degree of conversion has otherwise been achieved, the reaction mixture can be cooled and washed/extracted with an aqueous salt solution (e.g., brine) to remove catalyst residue. As already noted, the reaction mixture resulting from step Z3 typically includes the desired trans Compound X and by-product cis Compound X'. It is generally not necessary to separate and isolate Compound X for use in step Z4. Instead, the organic layer containing the trans/cis mixture is separated from the aqueous brine, and can then be dried and filtered, and the filtered solution concentrated or diluted or maintained at its existing concentration for use in Step Z4.

In a preferred aspect of the present invention, step Z3 comprises contacting diazo compound 9 of Formula:

9

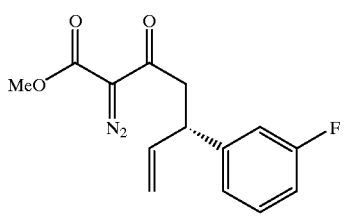

with a copper catalyst (e.g., a catalyst selected from $[(CH_3CN)_4Cu]PF_6$, $Cu(OTf)_2$, and CuCl+AgOTf), in an organic solvent (e.g., DCE, TCE, toluene, or THF), at a temperature (e.g., in a range of from about 70 to about 100° C.) suitable to form

10

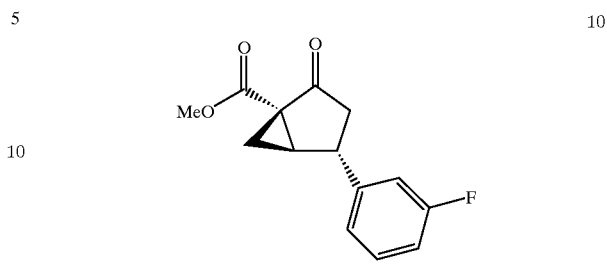

Step Z2. In another embodiment of the invention, the process for preparing 3-hydroxymethylcyclopentanone compounds of Formula (XII) comprises, in addition to steps Z3, Z4, Z5, and optionally Z6, as set forth above, a step Z2, which comprises reacting a beta-ketoester of Formula (VIII):

(VIII)

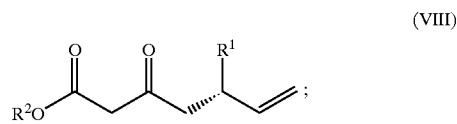

with a hydrocarbyl-sulfonyl azide or a substituted hydrocarbyl-sulfonyl azide in an organic solvent and in the presence of a base to form Compound IX.

In one embodiment, the sulfonyl azide is of formula $R^3SO_2N_3$;

wherein $R^3$ is $C_1$–$C_4$ alkyl, phenyl, or substituted phenyl, wherein each substituent on the substituted phenyl is independently selected from $C_1$–$C_{18}$ alkyl, $C_1$–$C_{18}$ haloalkyl, halo, cyano, nitro, $C_1$–$C_6$ alkoxy, $C_2$–$C_8$ alkoxyalkyl, $N(R^cR^d)_2$, and $NR^cCOR^d$; wherein each $R^c$ and $R^d$ is independently hydrogen, $C_1$–$C_6$ alkyl, or $(CH_2)_{0-4}CF_3$. In one aspect of the preceding embodiment, $R^3$ is phenyl or substituted phenyl, wherein each substituent on the substituted phenyl is independently selected from $C_1$–$C_{12}$ alkyl, $N(R^cR^d)_2$, and $NR^cCOR^d$; wherein each $R^c$ and $R^d$ is independently hydrogen or $C_1$–$C_4$ alkyl. In a further aspect of the preceding embodiment, the sulfonyl azide is selected from the group consisting of benzenesulfonyl azide, p-toluenesulfonyl azide, dodecylbenzenesulfonyl azide, and p-acetamidobenzenesulfonyl azide.

The azide and Compound VIII can be employed in any proportion which will result in the formation of at least some of Compound IX. The amount of azide employed in step Z2 can be, for example, at least about 0.5 equivalent (e.g., at least about 1 equivalent) per equivalent of Compound VIII, and is typically in the range of from about 1 to about 5 (e.g., from about 1 to about 3) equivalents per equivalent of Compound VIII. In one embodiment, the azide is present in an amount of from about 1 to about 2 (e.g., from about 1 to about 1.5) equivalents per equivalent of Compound VIII.

Suitable solvents for step Z2 include, but are not limited to, linear and branched halogenated alkanes, aliphatic nitriles, ethers and di-ethers, and aromatic hydrocarbons. Exemplary solvents include chloroform, carbon tetrachloride, methylene chloride, DCE, TCE, 1,1,2,2-teterachloroethane, 1,1-dichloroethane, acetonitrile, propionitrile, valeronitrile, ethyl ether, DME, MTBE, THF, dioxane, toluene and the xylenes. In one embodiment, the solvent is selected from the group consisting of $C_1$–$C_6$ linear and branched halogenated alkanes and $C_2$–$C_6$ aliphatic nitrites. In another embodiment, the solvent is a $C_1$–$C_6$ linear and branched halogenated alkane. In a preferred aspect of the preceding embodiment, the solvent is methylene chloride or DCE.

The base can be any organic or inorganic base. In one embodiment, the base is selected from the group consisting of tri-($C_1$–$C_4$ alkyl)amines, N-($C_1$–$C_4$ alkyl)-$C_3$–$C_6$ azacycloalkanes, and N-($C_3$–$C_4$ alkyl)oxazines. Exemplary bases of the preceding embodiment include triethylamine, trimethylamine, tri-n- or iso-propylamine, DIPEA, N-methylpiperidine, N-ethylpiperidine, and N-methylmorpholine. In a preferred aspect of the preceding embodiment, the base is a tri-($C_1$–$C_4$ alkyl)amine.

The base is suitably present in any proportion with respect to Compound VIII which will result in the formation of at least some of Compound IX. The base is typically present in an amount of from about 1 to about 5 equivalents per equivalent of Compound VIII. In one embodiment, the base is present in an amount of from about 1 to about 3 (e.g., from about 1.1 to about 2) equivalents per equivalent of Compound VIII.

Step Z2 is suitably conducted at a temperature in the range of from about −10 to about 35° C. (e.g., from about −5 to about 30° C.), and is typically conducted at a temperature in the range of from about 0 to about 25° C. In one embodiment, the temperature is in the range of from about 0 to about 20° C. (e.g., from about 0 to about 15° C.).

The reactants can be added to the reaction vessel in Z2 concurrently, either together or separately, or they can be added sequentially in either order. The solvent can be added before, during, or after addition of Compound VIII or the sulfonyl azide or both Compound VIII and the azide. Typically, Compound VIII pre-mixed with the solvent is charged to the reaction vessel followed by addition of the azide, optionally pre-mixed with a portion of solvent. The azide can be charged all at once at the start or can be added in portions or incrementally during the reaction.

In some instances (depending upon the sulfonyl azide and reaction conditions employed), by-product sulfonamide resulting from reaction Z2 can precipitate out of the reaction mixture and subsequently be removed by filtration. In other instances, the solution of Compound IX can be washed with aqueous HCl to remove base, after which the desired product can be separated from the sulfonamide by-product via chromatography or by trituration (e.g., with hexane to remove the sulfonamide). Because of the above-described safety hazards associated with Compound IX, the recovered solution of Compound IX is generally used directly in step Z4; i.e., Compound IX is generally not isolated in a purified form. The concentration of Compound IX in the solution can be adjusted as necessary for use in step Z4 by addition of more solvent or by evaporative removal of extant solvent.

Step Z1. In another embodiment of the invention, the process for preparing 3-hydroxymethylcyclopentanone compounds of Formula (XII) includes, in addition to steps Z2 to Z5, and optionally step Z6, as set forth above, a step Z1, which comprises reacting a compound of Formula (VI):

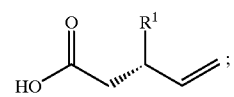

(VI)

with a malonate of Formula (VII):

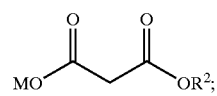

(VII)

in a solvent and in the presence of carbonyldiimidazole, a metal halide, and a base to form Compound VIII; wherein M is an alkali metal.

M can be any of the alkali metals of Group Ia of the Periodic Table, but is typically Na or K, and is more typically K. The metal malonate is commercially available, or can be prepared by reacting a mixture of the alkali metal amide (e.g., $NaNH_2$ or $KNH_2$) with the corresponding malonic monoester.

Suitable bases include, but are not limited to, primary, secondary, and tertiary alkyl amines, sodium carbonate, and potassium carbonate. In one embodiment, the base is a tri-($C_1$–$C_4$ alkyl)amine. In an aspect of the preceding embodiment the base is $Et_3N$.

The base, Compound VI, and Compound VII can be used in any proportions which will result in the formation of at least some of Compoud VIII. The base is typically present in an amount of from about 1 to about 4 equivalents per equivalent of Compound VII. In one embodiment, the base is present in an amount of from about 2 to about 4 equivalents per equivalent of Compound VII.

Compound VII is typically present in an amount of from about 1 to about 2 equivalents per equivalent of Compound VI. In one embodiment, Compound VII is present in an amount of from about 1.1 to about 2 equivalents per equivalent of Compound VI.

Suitable solvents for step Z1 include, but are not limited to, linear and branched halogenated alkanes, aliphatic nitriles, ethers and di-ethers, and aromatic hydrocarbons. Exemplary solvents include chloroform, carbon tetrachloride, methylene chloride, DCE, TCE, 1,1,2,2-teterachloroethane, 1,1-dichloroethane, acetonitrile, propionitrile, valeronitrile, ethyl ether, DME, MTBE, TBF, dioxane, toluene and the xylenes. In one embodiment, the solvent is selected from the group consisting of $C_1$–$C_6$ linear and branched halogenated alkanes and $C_2$–$C_6$ aliphatic nitriles. In another embodiment, the solvent is a $C_1$–$C_6$ linear and branched halogenated alkane. In a preferred aspect of the preceding embodiment, the solvent is methylene chloride or DCE.

The metal halide (i.e., fluoride, chloride, bromide, or iodide) can be a halide of any metal of Group IIa of the Periodic Table. In one embodiment, the halide is a magnesium halide, preferably magnesium chloride.

Step Z1 is suitably conducted at a temperature in the range of from about 0 to about 50° C. (e.g., from about 10 to about 50° C.), and is typically conducted at a temperature in the range of from about 10 to about 30° C. In one embodiment, the temperature is in the range of from about 15 to about 30° C. (e.g., from about 20 to about 25° C.).

The reaction generally requires a particular protocol: Solvent (e.g., $CH_2Cl_2$), Compound VII, and the metal chloride (e.g., MgCl$_2$) are charged to a reaction vessel, followed by addition of base (e.g., Et$_3$N). The resulting mixture is aged at low temperature (e.g., from about 0 to about 25° C.). A solution of activated Compound VI is formed in a separate vessel by mixing Compound VI with a solvent solution of CDI, wherein the addition is accompanied by the evolution of CO$_2$ gas. The solution of activated Compound VI can then be charged to the reaction vessel, the resulting mixture brought to reaction temperature, and the reaction conducted until the desired degree of conversion is achieved.

At the conclusion of the reaction, Compound VIII can be recovered by conventional means.

Step Y2. The present invention also includes a process for preparing a compound of Formula (V):

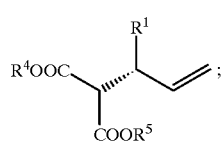

(V)

which comprises (Y2) reacting a carbonate of Formula (III):

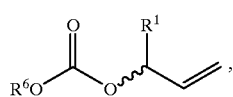

(III)

with the salt of a strong base selected from hydrides, C$_1$–C$_6$ alkoxides, amides, cyanides, and hexamethyldisilazides of alkali metals and a malonic ester of Formula (IV):

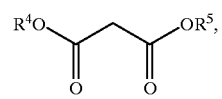

(IV)

in a reaction solvent and in the presence of a molybdenum catalyst to form a compound of Formula (V); wherein:

the molybdenum catalyst comprises a catalyst complex prepared by heating a mixture of a multi-dentate, N-containing chiral ligand and MO(CO)$_6$ in a catalyst-preparation solvent at a temperature in a range of from about 15 to about 120° C. for a time sufficient to form the catalyst complex; wherein the chiral ligand is present in an amount of from about 1 to about 2 equivalents per equivalent of MO(CO)$_6$;

R$^1$ is as heretofore defined;

R$^4$ and R$^5$ are each independently C$_1$–C$_4$ alkyl or C$_1$–C$_4$ haloalkyl; and R$^6$ is C$_1$–C$_4$ alkyl.

Step Y2 is an alkylation reaction in which the carbonate group —OCO$_2$R$^6$ on Compound III is displaced in the presence of a molybdenum catalyst complex with the salt of a malonate formed by reaction of Compound IV with strong base, to give Compound V. The reaction can have high regioselectivity; i.e., the reaction product will typically have an excess, often a substantial excess, of Compound V-1 over Compound V-2:

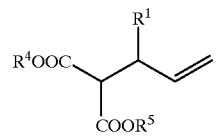

V-1

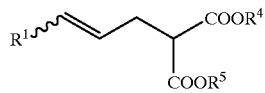

V-2

The reaction can also have a high enantiomeric excess (ee) of one optical isomer over another; i.e., the product will typically have an excess, often a substantial excess, of Compound V over Compound V':

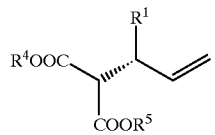

V

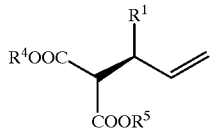

V'

In an embodiment of the process, R$^4$ and R$^5$ are each independently C$_1$–C$_4$ alkyl or (CH$_2$)$_{0-3}$CF$_3$. In another embodiment, R$^4$ is methyl, ethyl, CF$_3$, or CH$_2$CF$_3$, and R$^5$ is C$_1$–C$_4$ alkyl or (CH$_2$)$_{0-3}$CF$_3$. In an aspect of the preceding embodiment, R$^4$ is methyl or ethyl, and R$^5$ is C$_1$–C$_4$ alkyl. In another aspect of the preceding embodiment, each of R$^4$ and R$^5$ is independently methyl or ethyl. In still another aspect, R$^4$ and R$^5$ are both methyl.

Other embodiments of the process include Compound III, wherein R$^6$ is C$_1$–C$_3$ alkyl; or is methyl or ethyl; or is methyl. Still other embodiments of the process include Compound III, wherein R$^1$ is any one of the embodiments or aspects as earlier defined and described.

The malonate salt is suitably present in any proportion with respect to Compound III which will result in the formation of at least some of Compound V. The malonate salt of Compound IV is typically present in an amount of from about 1 to about 5 equivalents per equivalent of Compound III. In one embodiment, the salt is present in an amount of from about 1 to about 3 (e.g., from about 1 to about 2) equivalents per equivalent of Compound III.

The amount of catalyst employed in step Y2 is suitably at least about 0.001 equivalent of molybdenum per equivalent of Compound III, and is typically in a range of from about 0.01 to about 0.2 equivalents of Mo per equivalent of Compound III. In one embodiment, the catalyst is in an amount in a range of from about 0.1 to about 0.2 equivalents of Mo per equivalent of Compound III. Exemplifying the preceding embodiment is the use of the catalyst is in an amount in a range of from about 0.1 to about 0.15 equivalents of Mo per equivalent of Compound III.

Suitable reaction solvents include, but are not limited to, C$_3$–C$_{12}$ linear and branched alkanes, C$_1$–C$_6$ linear and branched halogenated alkanes, C$_5$–C$_7$ cycloalkanes, C$_6$–C$_{10}$ aromatic hydrocarbons, dialkyl ethers wherein each alkyl is independently a C$_1$–C$_6$ alkyl, C$_4$–C$_8$ dialkoxyalkanes, $C_4$–$C_6$ cyclic ethers and diethers, $C_6$–$C_8$ aromatic ethers, $C_1$–$C_6$ alkyl esters of $C_1$–$C_6$ alkylcarboxylic acids, and N,N, di-$C_1$–$C_6$ alkyl amides of $C_1$–$C_6$ alkylcarboxylic acids. Examples of the foregoing solvents include hexane, heptane, carbon tetrachloride, chloroform, methylene chloride, 1,2-dichloroethane (DCE), 1,1,2-trichloroethane (TCE), cyclohexane, toluene, o- and m- and p-xylene, ethylbenzene, ethyl ether, MTBE, THF, dioxane, 1,2-dimethoxyethane (DME), anisole, phenetole, methyl acetate, ethyl acetate, isopropyl acetate, DMF, and DMA. In one embodiment, the solvent is a $C_2$–$C_4$ chlorinated alkane or a $C_7$–$C_{10}$ aromatic hydrocarbon. In an aspect of the preceding embodiment, the solvent is DCE or toluene. In another aspect, the solvent is toluene.

Step Y2 is suitably conducted at a temperature in the range of from about 15 to about 120° C. (e.g., from about 25 to about 110° C.), and is typically conducted at a temperature in the range of from about 60 to about 100° C. In one embodiment, the temperature is in the range of from about 80 to about 100° C. (e.g., from about 90 to about 95° C.).

The reactants can be added to the reaction vessel in Z1 concurrently, either together or separately, or they can be added sequentially in any order. In a typical procedure, the malonate salt IV and solvent are charged to a reaction vessel, followed by addition of the carbonate III in solvent. A separately prepared catalyst solution is then added, and the mixture brought to reaction temperature.

At the conclusion of the reaction, the mixture can be worked up via conventional techniques.

Malonate salt. The alkali metal salt of malonic ester IV can be prepared by heating a mixture of IV, solvent, and a strong base. Suitable bases include, but are not limited to, the hydrides (e.g., NaH or KH), hydroxides (e.g., NaOH or KOH), $C_1$–$C_6$ alkoxides (e.g., NaO-t-Bu or NaOEt), amides (e.g., LDA), and hexamethyldisilazides (e.g., LHMDS or NaHMDS) of the alkali metals. The base is typically NaH. The solvent is an organic solvent, and is typically an ether or an aromatic hydrocarbon; i.e., any of the aliphatic and cyclic ethers and di-ethers and aromatic hydrocarbons described elsewhere in this specification as solvents. A preferred solvent is THF. Another preferred solvent is toluene. The mixture is typically heated to a temperature in a range of from about 50 to about 90° C. for a time sufficient to form the malonate salt. The resulting mixture of malonate salt can be used directly in step Y2 without further treatment. If desired, the malonate salt can be isolated prior to use in step Y2 by cooling the reaction mixture to room temperature, and filtering and drying the precipitated salt.

Molybdenum catalyst complex. The molybdenum catalyst complex can be prepared by heating a mixture of a chiral ligand and Mo(CO)$_6$ in a solvent, wherein the chiral ligand is typically employed in an amount of from about 1 to about 3 (e.g., from about 1 to about 2) equivalents per equivalent of Mo(CO)$_6$. The solvent is suitably a solvent selected from the group consisting of $C_4$–$C_{10}$ aliphatic ethers and diethers, $C_4$–$C_6$ cyclic ethers and diethers, $C_2$–$C_6$ linear and branched halogenated alkanes, and $C_6$–$C_{10}$ aromatic hydrocarbons. In one embodiment, the solvent is a $C_2$–$C_6$ linear or branched halogenated alkane. Exemplary halogenated solvents are DCE and methylene chloride. DCE is a preferred halogenated solvent. In another embodiment, the solvent is a $C_6$–$C_{10}$ aromatic hydrocarbon. Exemplary aromatic hydrocarbon solvents include, but are not limited to, benzene, toluene, the o- and m- and p-xylenes, ethylbenzene, naphthalene, and the methyl- and dimethylnaphthalenes. Toluene is a preferred aromatic hydrocarbon solvent. The mixture is suitably heated to a temperature up to and including the reflux temperature of the solvent. Typically the temperature is in a range of from about 15 to about 120° C. (e.g., from about 25 to about 100° C.). In one embodiment, the temperature is in a range of from about 60 to about 100° C. In an aspect of the preceding embodiment, the temperature is from about 70 to about 90° C. (e.g., from about 75 to about 90° C.). The heating time can vary widely depending upon the choice of ligand and solvent, the amounts of ligand and solvent and Mo(CO)$_6$, and the heating temperature. Nonetheless, the heating time is often in the range of from about 0.25 to about 10 hours. Exemplary heating times include times in ranges of from about 0.5 to about 8 hours, from about 2 to about 4 hours, and from about 0.5 to about 4 hours. In preparing the catalyst complex, Mo(CO)$_6$ and ligand are typically mixed together in a reaction vessel under an inert atmosphere (e.g., nitrogen or argon), followed by addition of solvent, and the resulting solution under an inert atmosphere is brought to reaction temperature.

The molybdenum catalyst complex represents a key advantage of the process of the present invention. The complex is prepared directly from the chiral ligand and Mo(CO)$_6$ which is stable and inexpensive. By contrast, known processes require two steps, wherein Mo(CO)$_6$ is first reacted with an organic ligand to form a coordination compound, and the coordination compound is then complexed with a chiral ligand to provide a suitable Mo chiral catalyst complex. It is known, for example, to heat Mo(CO)$_6$ with proprionitrile and cycloheptatriene respectively to obtain $(C_2H_5CN)_3Mo(CO)_3$ and (cycloheptatrienyl)$_3$Mo(CO)$_3$, each of which can then be reacted with a chiral ligand. $(C_2H_5CN)_3Mo(CO)_3$ is not commercially available and is less stable (e.g., will oxidize more quickly) than Mo(CO)$_6$. (Cycloheptatrienyl)Mo(CO)$_3$ has limited commercial availability, and is expensive.

The Chiral Ligand. The chiral ligand is a multi-dentate, N-containing chiral ligand. In one embodiment, the chiral ligand is also a $C_2$-symmetric ligand. Suitable ligands include, but are not limited to, bis-oxazolines such as those described above in the discussion of catalysts employed in step Z3. Also suitable as chiral ligands are bis-amides such as the N,N'-bis-pyridinecarboxamides described in Barnes et al., *J. Chem. Eng. Data* 1978, 23: 349–350. In one embodiment, the chiral ligand is

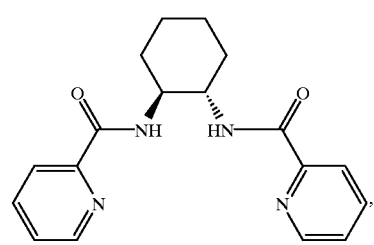

L1

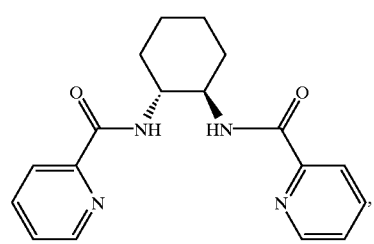

L2

L3
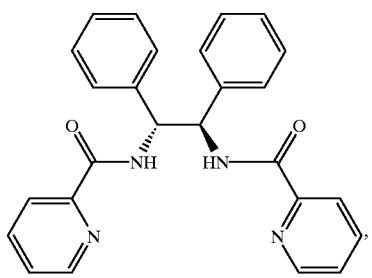
L4
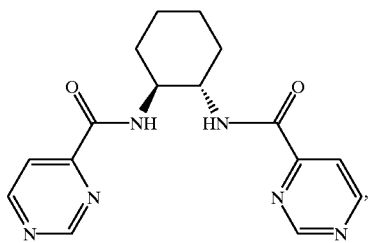
L5
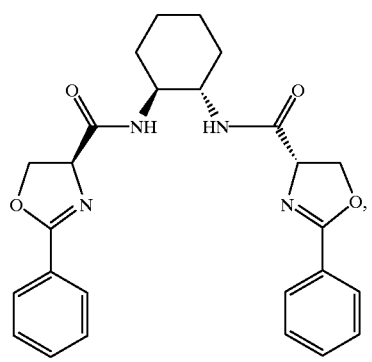
L6
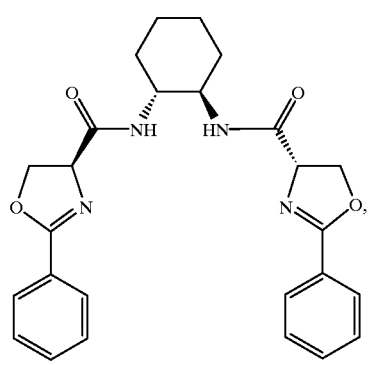
L7
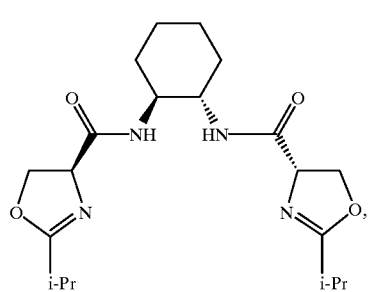
L8
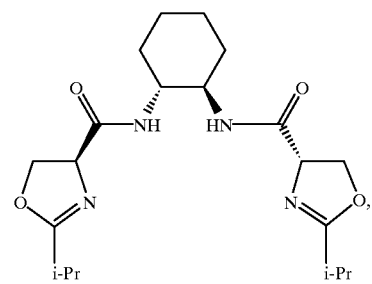
L9
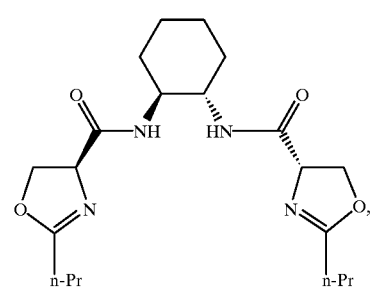
L10
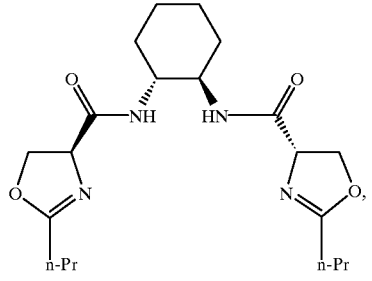
L11
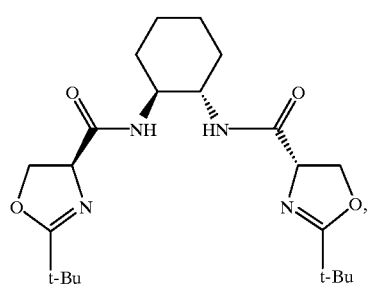
L12
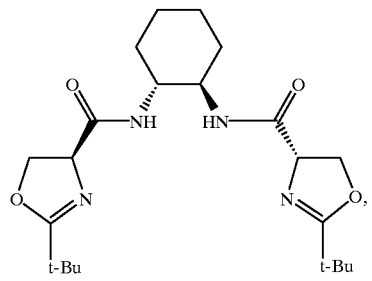

-continued

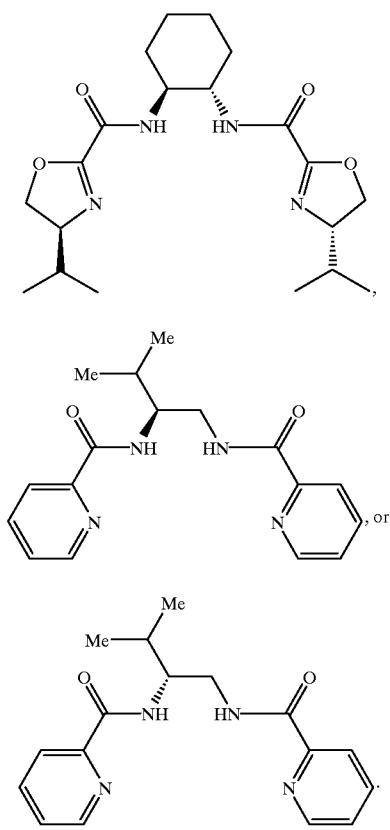

In an aspect of the preceding embodiment, the chiral ligand is the S,S-ligand L1. L1 can be prepared in good yield by contacting an activated solution of 2-pyridinecarboxylic acid with (1S,2S)-1,2-diaminocyclohexane at a temperature in a range of from about 0 to about 60° C. for a time sufficient to form L1; wherein the activated solution of 2-pyridinecarboxylic acid is formed by treating 2-pyridinecarboxylic acid in admixture with organic solvent with CDI. 2-Pyridine carboxylic acid is suitably employed in the preparation in an amount of about 2 or more equivalents per equivalent of (1S,2S)-1,2-diaminocyclohexane, and CDI is suitably employed in an amount of about 0.5 or more equivalents per equivalent of 2-pyridinecarboxylic acid. In the typical preparation of L1, the amount of 2-pyridinecarboxylic acid is in a range of from about 2 to about 3 (e.g., from about 2.1 to about 2.7) equivalents per equivalent of (1S,2S)-1,2-diaminocyclohexane; and the temperature is in a range of from about 0 to about 50° C. (e.g., from about 15 to about 50° C.). In the typical preparation of the activated solution of 2-pyridinecarboxylic acid, the amount of CDI is in a range of from about 0.8 to about 1.5 (e.g., from about 1 to about 1.5) equivalents per equivalent of 2-pyridinecarboxylic acid; the solvent is an ether (e.g., THF); and the temperature is in a range of from about 0 to about 25° C. (e.g., from about 10 to about 20° C.). At the conclusion of the reaction, the solvent is removed from the reaction mixture to recover L1, followed by crystallization, e.g., from ethanol. Yields of at least about 80% can be achieved.

The present invention includes the method of preparing the ligand L1 as set forth in the preceding paragraph. However, ligand L1 can alternatively be prepared for use in step Y2 in accordance with the procedure set forth in Barnes et al., *J. Chem. Eng. Data* 1978, 23: 349–350. The method of the invention is superior to the method as described in Barnes et al. in terms of the scalability of the preparation and the purity of the resulting L1.

Step Y1. In another embodiment of the process for preparing a compound of Formula (V), the process further comprises step Y1, which is mixing a solution of vinylmagnesium halide in an ether or in an aromatic hydrocarbon with an aldehyde of Formula (I):

$R^1$—CHO (I), and then treating the mixture with a trapping agent of Formula (II):

 (II)

to form Compound III; wherein Q is halo and $R^6$ is as defined above.

The vinylmagnesium halide can be represented as

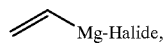

wherein Halide is fluoride, chloride, bromide, or iodide. The halide is typically chloride or bromide. The ether employed to form the magnesium halide solution is suitably an aliphatic $C_2$–$C_6$ ether or di-ether or a $C_4$–$C_6$ cyclic ether or di-ether. Suitable ethers include, but are not limited to, ethyl ether, MTBE, THF and dioxane.

The vinylmagnesium halide can be employed in any proportion with respect to aldehyde I which will result in the formation of at least some of Compound III. The vinylmagnesium halide is typically employed in an amount of from about 0.9 to about 3 equivalents per equivalent of aldehyde I. In one embodiment, the amount of vinylmagnesium halide employed is in a range of from about 1.5 to about 3 (e.g., 1.05 to about 1.5) equivalents per equivalent of I. In another embodiment, the amount of halide is from about 0.95 to about 2 equivalents per equivalent of I.

The ether solution and aldehyde I are suitably mixed at a temperature in a range of from about −80 to about 30° C., and typically at a temperature in a range of from about −10 to about 25° C. In one embodiment of step Y1, the temperature is in a range of from about 0 to about 10° C. (e.g., from about 0 to about 5° C.). When mixing is complete, the temperature of the mixture can be raised (e.g., an increase of from about 5 to about 15° C.) in order to increase reaction rate.

In one embodiment, in the trapping agent of Formula (II) employed in step Y1, Q is bromo or chloro and $R^6$ is methyl or ethyl. In one aspect, the trapping agent is methyl chloroformate. Treating the mixture with the trapping agent typically involves adding about 1 or more equivalents of trapping agent per equivalent of vinylmagnesium halide (e.g., from about 1 to about 2 equivalents of trapping agent per equivalent of Grignard) to the mixture while maintaining the mixture at a temperature as set forth in the preceding paragraph. After addition of the agent has been completed, the temperature of the mixture can be raised (e.g., by about 5 to about 15° C.) in order to increase the reaction rate.

The reaction mixture is quenched and carbonate III can be recovered by adding water and optionally more solvent to the mixture, separating the organic and aqueous layers, washing the organic layer with brine, drying, and removing the solvent by, e.g., vacuum evaporation.

Steps Y3 and Y3'. The present invention also includes a process for preparing a carboxylic acid of Formula (VI):

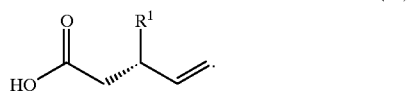
(VI)

which comprises step Y2 as set forth above and a step Y3, which is heating Compound V with an aqueous acid, optionally in admixture with one or more co-solvents, to form compound VI.

In step Y3, the aqueous acid is suitably an aqueous solution of a mineral acid such as hydrochloric acid, sulfuric acid, or nitric acid. In one embodiment, the aqueous acid is 1N to 6N HCl.

Co-solvent can be included in order to provide a homogeneous reaction mixture by providing a medium in which both Compound V and the aqueous acid are soluble or at least intimately dispersible. Suitable co-solvents are polar organic solvents which include, but are not limited to, $C_1$–$C_6$ monohydric alcohols (e.g., methanol, ethanol, n-propanol, n-butanol, n-pentanol, isopropanol, and sec-butyl alcohol), $C_2$–$C_8$ polyhydric alcohols (e.g., ethylene glycol, propylene glycol, and glycerol), $C_1$–$C_4$ nitriles (e.g., acetonitrile and propionitrile), ), aliphatic $C_2$–$C_6$ ethers and di-ethers (e.g., ethyl ether, MTBE and dimethoxyethane), $C_4$–$C_6$ cyclic ethers and di-ethers (e.g., THF and dioxane), DMF, and DMSO. In one embodiment, the co-solvent is selected from the group consisting of aliphatic $C_2$–$C_6$ ethers and di-ethers and $C_4$–$C_6$ cyclic ethers and di-ethers. In an aspect of the preceding embodiment, the co-solvent is THF or dioxane.

The reaction mixture is suitably heated to and maintained at a temperature in a range of from about 40 to about 120° C., and is typically heated at reflux.

The present invention includes another process for preparing a carboxylic acid of Formula (VI):

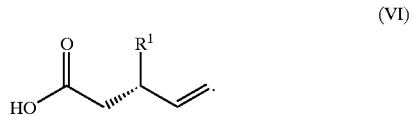
(VI)

which comprises step Y2 as set forth above and a step Y3', which is contacting Compound V with aqueous base, optionally in admixture with one or more co-solvents, at a temperature in a range of from about 20° C. to reflux (e.g., from about 20 to about 120° C.) to form a mixture containing hydrolyzed Compound V, and then acidifying the mixture to a pH of less than about 6 and heating to form a carboxylic acid of Formula (VI).

Step Y3' consists of base hydrolysis of Compound V followed by acid decarboxylation. Suitable bases for the hydrolysis include, but are not limited to, alkali metal hydroxides (e.g., LiOH, NaOH and KOH) and alkaline earth metal hydroxides (e.g., $Mg(OH)_2$, $Ca(OH)_2$, and $Ba(OH)_2$). Very dilute to very concentrated solutions of the base can be employed. In one embodiment, the aqueous base is 0.001N to 12N NaOH. Suitable co-solvents are the same as those defined and described above for Step Y3. The hydrolysis is suitably conducted at a temperature in a range of from about 0 to about 120° C., and typically at a temperature in a range of from about 25 to about 80° C. In one embodiment, the hydrolysis is conducted at reflux.

The mixture containing hydrolyzed V is acidified with a strong acid (e.g., hydrochloric, sulfuric, or nitric acid) to a pH of less than about 7. The pH is typically in a range of from about 0.5 to about 6. In one embodiment, the pH is in a range of from about 0.5 to about 4. In an aspect of the preceding embodiment, the pH is from about 0.5 to about 2. In another embodiment the pH is less than about 2; e.g., from about 0.5 to 1.5.

The acidified mixture is suitably heated to and maintained at a temperature in a range of from about 40 to about 120° C., and is typically heated at reflux.

In both steps Y3 and Y3', removal of the by-product alcohol(s) (i.e., $R^4OH$ and $R^5OH$) during hydrolysis (e.g., by distillation), can promote completion of the reaction. Upon completion of the reaction, the reaction mixture can be cooled, extracted with organic solvent (e.g., toluene), and the organic extract containing Compound VI can be dried. Compound VI can be recovered and isolated by amine salt formation; i.e., by contacting a suitable portion of amine with Compound VI to form an amine salt, reconverting the amine salt to acid VI by partitioning with an aqueous strong base (e.g., NaOH) and an organic solvent (e.g., a haloalkane such as $CH_2Cl_2$, an alkyl carboxylate such as EtOAc or IPAc, an ether such as THF or MTBE, or an aromatic hydrocarbon such as toluene), followed by acidification with a strong acid (e.g., HCl), and extraction with an organic solvent such as those described earlier in this sentence. Suitable amines include, but are not limited to, dicyclohexylamine, dibenzylamine, dibenzyl ethylenediamine, benzylamine, (S)-phenethylamine, and (R)-phenethylamine.

The present invention also includes the following processes:

a process for preparing a carboxylic acid of Formula (VI) which comprises each of the steps Y1, Y2 and Y3, as heretofore defined and described;

a process for preparing a carboxylic acid of Formula (VI) which comprises each of the steps Y1, Y2 and Y3', as heretofore defined and described;

a process for preparing a hydroxymethylcyclopentanone compound of Formula (XII) which comprises each of the steps Y1, Y2, Y3, and Z1 to Z5, and optionally Z6, as heretofore defined and described; and a process for preparing a hydroxymethylcyclopentanone compound of Formula (XII) which comprises each of the steps Y1, Y2, Y3', and Z1 to Z5, and optionally Z6, as heretofore defined and described.

If desired, the progress of the reaction in any of the above-described reaction steps can be followed by monitoring the disappearance of a reactant (e.g., Compound X in step Z4) and/or the appearance of the product (e.g., Compound XII in step Z5) using TLC, HPLC, NMR or GC.

The present invention also includes a compound selected from the group consisting of:

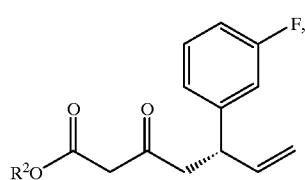

-continued

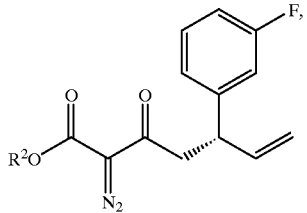

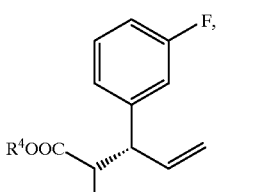

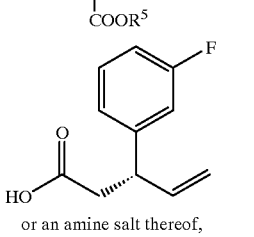

or an amine salt thereof,

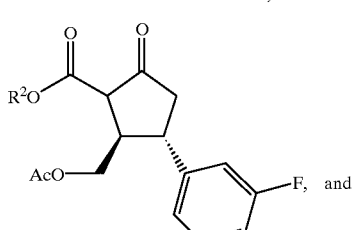

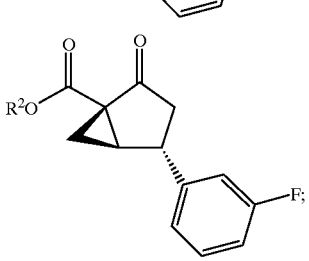

wherein $R^2$, $R^4$ and $R^5$ are each independently as defined above. In one embodiment, the compound is selected from the group of compounds as defined above, wherein each of $R^2$, $R^4$ and $R^5$ is independently methyl or ethyl. In another embodiment, the compound is selected from the group of compounds as defined above, wherein each of $R^2$, $R^4$ and $R^5$ is methyl.

Each of the following compounds is an aspect of the present invention:

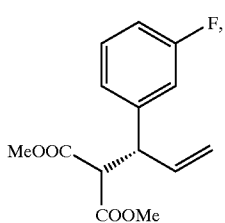

-continued

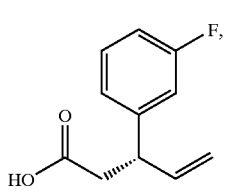

or an (S)-α-methylbenzylamine salt thereof,

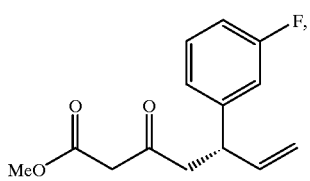

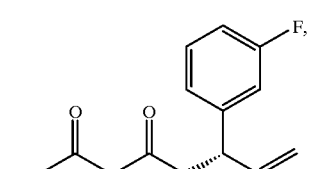

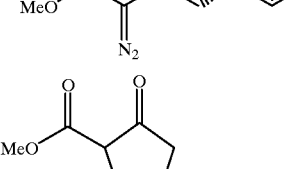

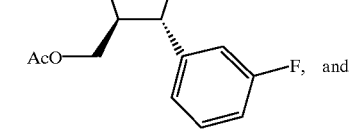

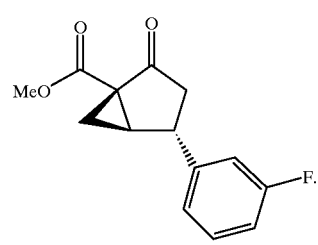

As used herein, the term "$C_1$–$C_{10}$ alkyl" (which may alternatively be referred to herein as "$C_{1-10}$ alkyl") means linear or branched chain alkyl groups having from 1 to 10 carbon atoms and includes all of the decyl alkyl, nonyl alkyl, octyl alkyl, heptyl alkyl, etc. isomers. Similarly, the term "$C_1$–$C_6$ alkyl" (or "$C_{1-6}$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl. Similar terms (e.g., "$C_1$–$C_3$ alkyl") have analogous definitions.

The term "$C_2$–$C_{10}$ alkenyl" (or "$C_{2-10}$ alkenyl") means linear or branched chain alkenyl groups having from 2 to 10 carbon atoms and includes all of the decyl alkenyl, nonyl alkenyl, octyl alkenyl, heptyl alkenyl, etc. isomers. Similarly, the term "$C_2$–$C_6$ alkenyl" means linear or branched chain alkenyl groups having from 2 to 6 carbon atoms and includes all of the hexyl alkenyl and pentyl alkenyl isomers as well as 1-, 2- and 3-butenyl, 1- and 2-isobutenyl, 1- and 2-propenyl, and ethenyl. "$C_2$–$C_4$ alkenyl" has an analogous definition.

The term "$C_2$–$C_{10}$ alkynyl" means linear or branched chain alkynyl groups having from 2 to 10 carbon atoms and includes all of the decyl alkynyl, nonyl alkynyl, octyl alkynyl, heptyl alkynyl, etc. isomers. The term "$C_2$–$C_6$ alkynyl" means linear or branched chain alkynyl groups having from 2 to 6 carbon atoms and includes all of the hexyl alkynyl and pentyl alkynyl isomers as well as 1-, 2- and 3-butynyl, 1- and 2-propynyl, and ethynyl. Similar terms (e.g., "$C_2$–$C_4$ alkynyl") have analogous definitions.

The term "$C_1$–$C_6$ alkoxy" means an —O-alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similar terms (e.g., "$C_1$–$C_3$ alkoxy") have analogous definitions.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Similarly, "$C_2$–$C_6$ alkoxyalkyl" means a linear or branched $C_1$–$C_5$ alkyl group as defined above having as a substituent a $C_1$–$C_5$ alkoxy group as defined above, wherein the alkoxyalkyl group has a total of from 2 to 6 carbon atoms. "$C_2$–$C_4$ alkoxyalkyl" means a linear or branched $C_1$–$C_3$ alkyl group as defined above having as a substituent a $C_1$–$C_3$ alkoxy group as defined above, wherein the alkoxyalkyl group has a total of from 2 to 4 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3, (CH_2)_{1-4}OCH_3, (CH_2)_{1-3}OCH_3, (CH_2)_{1-6}OCH_2CH_3$, and $(CH_2)_{1-4}OCH_2CH_3$.

The term "$C_3$–$C_8$ cycloalkyl" refers to a cyclic ring selected from cyclopropyl, cyclobutyl, cyclopentyl, cyclohexyl, cycloheptyl, and cyclooctyl. The term "$C_3$–$C_6$ cycloalkyl" refers to a cyclic ring selected from cyclopropyl, cyclobutyl, cyclopentyl, and cyclohexyl. Similar terms (e.g., "$C_5$–$C_6$ cycloalkyl") have analogous definitions.

The term "halogen" (which may alternatively be referred to as "halo") refers to fluorine, chlorine, bromine and iodine (alternatively, fluoro, chloro, bromo, and iodo).

The term "halogenated $C_1$–$C_6$ alkyl" (which may alternatively be referred to as "$C_1$–$C_6$ haloalkyl" or "$C_{1-6}$ haloalkyl") means a $C_1$ to $C_6$ linear or branched alkyl group as defined above with one or more halogen substituents. The terms "halogenated $C_1$–$C_4$ alkyl" and "halogenated $C_1$–$C_3$ alkyl" have analogous meanings. The term "fluorinated $C_1$–$C_6$ alkyl" (or "$C_1$–$C_6$ fluoroalkyl" or "$C_{1-6}$ fluoroalkyl") means a $C_1$ to $C_6$ linear or branched alkyl group as defined above with one or more fluorine substituents. The terms "fluorinated $C_1$–$C_4$ alkyl" and "fluorinated $C_1$–$C_3$ alkyl" have analogous meanings. Representative examples of suitable fluoroalkyls include the series $(CH_2)_{0-3}CF_3$ and $(CH_2)_{0-2}CF_3$ (i.e., trifluoromethyl, 2,2,2-trifluoroethyl, and 3,3,3-trifluoro-n-propyl), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "$C_1$–$C_6$ alkylcarboxylic acid" refers to a compound of formula $R^o$—COOH, wherein $R^o$ is $C_1$–$C_6$ linear or branched alkyl group as defined above. Similarly, "$C_1$–$C_6$ thioalcohol" means a compound of formula $R^o$—SH, and "$C_1$–$C_6$ alkylamine" means a compound of formula $R^o$—$NH_2$. The term "$C_1$–$C_6$ alkoxide" refers to the anion O—$R^o$.

The term "substituted" includes mono- and poly-substitution by a named substituent to the extent such single and multiple substitution is chemically allowed and results in a chemically stable compound. Thus, for example, the term "substituted phenyl" in the definition of $R^1$ encompasses mono-, di-, tri-, tetra-, and penta-substitution of the phenyl moiety by one or more of the named substituents. As another example, the term "substituted heterocycle" in the definition of $R^1$ can have mono-, di-, tri-, tetra-, penta- or higher substitution (e.g., from 1 to 7 substituents), wherein the maximum number of substituents depends upon the number of sites available on the particular heterocyclic ring system.

"Hydrocarbyl" means a radical having a carbon atom directly attached to the remainder of the molecule and consisting of one or more carbon atoms and hydrogen atoms. Hydrocarbyl radicals include aliphatic hydrocarbyl groups (e.g., alkyl, alkenyl, or alkynyl), alicyclic hydrocarbyl (e.g., cycloalkyl or cycloalkenyl), aliphatic hydrocarbyl substituted alicyclic hydrocarbyl (e.g., alkyl-substituted cycloalkyl or alkenyl-substituted cycloalkyl), alicyclic hydrocarbyl substituted aliphatic hydrocarbyl (e.g., cycloalkyl-substituted alkyl or cycloalkyl-substituted alkenyl), aromatic hydrocarbyl (e.g., phenyl or naphthyl), aliphatic- and alicyclic-substituted aromatic, aromatic-substituted aliphatic or alicyclic, and the like. The hydrocarbyl radical suitably contains from 1 to about 40 carbon atoms, and typically contains from 1 to about 30 carbon atoms (e.g., from 1 to about 20 carbon atoms, or from 1 to about 12 carbon atoms).

"Substituted hydrocarbyl" means a hydrocarbyl radical as defined in the preceding paragraph, wherein one or more of the hydrogen atoms have been replaced by one or more heteroatom-containing substituents such as halogen, hydroxy (—OH), mercapto (—SH), oxo (=O), alkoxy (—O-alkyl), primary amino (—$NH_2$), N-alkylamino (—NH-alkyl), N,N-dialkylamino (—N(alkyl)$_2$), carboxamido (—C(=O)$NH_2$), carboxy (—COOH), alkoxycarbonyl (—C(=O)O-alkyl), alkylcarbonyl (C(=O)-alkyl), formyl (—CHO), nitro (—$NO_2$), cyano (—CN), and the like.

The term "heterocycle" (which may alternatively be referred to as "heterocyclic") refers to a 4- to 8-membered monocyclic ring or 7- to 11-membered bicyclic ring system, any ring of which is saturated or unsaturated, and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure.

The term "heterocycle" as used herein is intended to include the following groups: benzoimidazolyl, benzofuranyl, benzofurazanyl, benzopyrazolyl, benzotriazolyl, benzothiophenyl, benzoxazolyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "alkali metal" refers to a metal of Group Ia of the Periodic Table, including but not limited to lithium, sodium, and potassium.

The term "solvent" refers to a substance which under the conditions of the particular reaction step in which it is employed is chemically inert and can dissolve, disperse, and/or suspend, and thereby bring into contact, the reactants and any other reagents involved in the reaction.

Abbreviations used in the instant specification include the following:

Ac=acetic or acetate
AcOH=acetic acid
AIDS=acquired immune deficiency syndrome
ARC=AIDS related complex
Bn=benzyl
Boc or BOC=t-butyloxycarbonyl
Bu=butyl
CBZ=carbobenzoxy (=benzyloxycarbonyl)
CDI=carbonyldiimidazole
DCE=1,2-dichloroethane
DIEA or DIPEA=diisopropylethylamine
DMA=dimethylacetamide
DMF=dimethylformamide
DME=1,2-dimethoxyethane
DMPU=N, N'-dimethylpyrimidinone
DMSO=dimethylsulfoxide
dppe=1,2-bis(diphenylphosphino)ethane
Et=ethyl
Et₃N=triethylamine
HPLC=high performnance liquid chromatography
IPAc=isopropyl acetate
KF=Karl Fisher titration for water
LAH=lithium aluminum hydride
LHMDS=lithium hexamethyldisilazide
MTBE=methyl t-butyl ether
NaHMDS=sodium hexamethyldisilazide
Me=methyl
MEK=methyl ethyl ketone
NMP=N-methylpyrrolidone
NMR=nuclear magnetic resonance
OAc=acetate
OTf=triflate
Ph=phenyl
PMB=para-methoxybenzyl
Pr=propyl
TBAF=tetrabutylammonium fluoride TBDMS-Cl=t-butyldimethylsilyl chloride
TBDMSO=t-butyldimethyloxysilyloxy
TCE=1,1,2-trichloroethane
Tf=triflic (=trifluoromethanesulfonyl)
TFA=trifluoroacetic acid
THF=tetrahydrofuran
TLC=thin layer chromatography
TMS=trimethylsilyl
TPAP=tetrapropylammonium perruthenate The following schemes disclose methods for preparing piperdinylmethyl-cyclopentyl compounds useful as CCR5 antagonists starting with the hydroxymethylcyclopentanone compounds of Formula (XII) which can be prepared from the processes of the present invention.

SCHEME 1

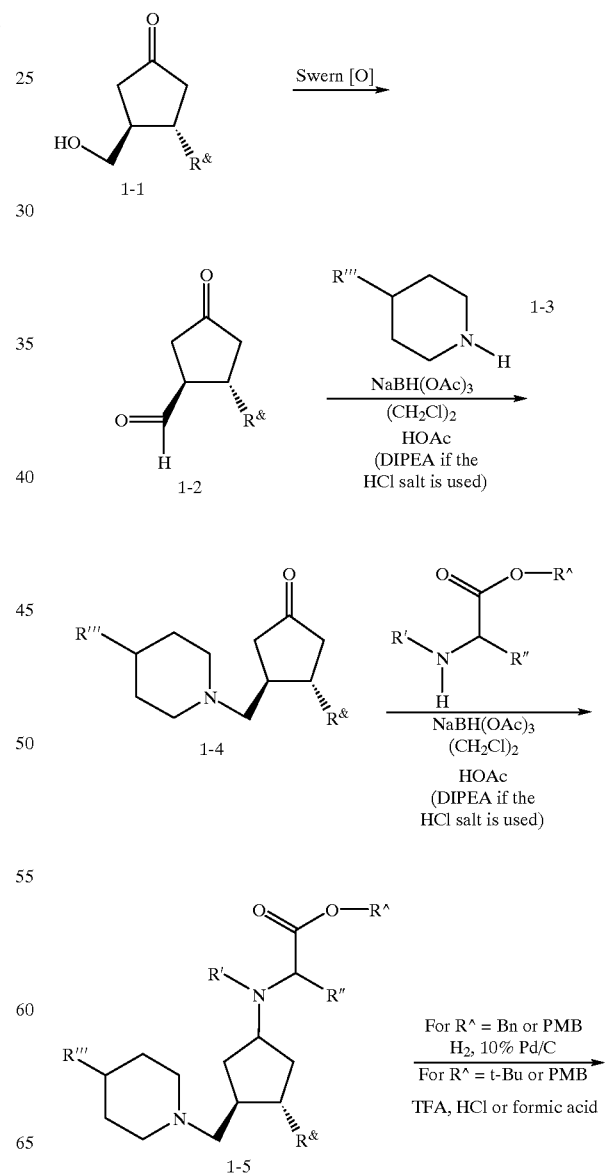

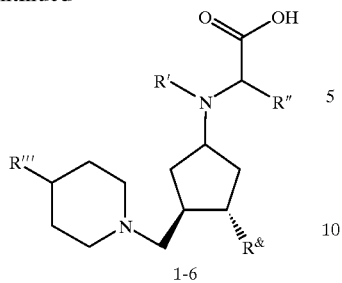

1-6

A route for the preparation of some 1,3,4-trisubstituted cyclopentanes useful as CCR5 antagonists is given in Scheme 1. Oxidation to the ketone-aldehyde 1-2 can be carried out under numerous conditions, such as with DMSO and oxalyl chloride at low temperature followed by triethylamine (Swern oxidation), with the Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Selective reductive alkylation of the 4-substituted piperidine 1-3 with the aldehyde of 1-2, using for example sodium triacetoxyborohydride or sodium cyanoborohydride in a suitable solvent such as methylene chloride, 1,2-dichloroethane, THF, acetonitrile or methanol, then provides the 3-((4-substituted piperidin-1-yl)methyl) cyclopentane derivative 1-4. A reductive alkylation of a D- and/or L-amnino-acid ester, such as the methyl, ethyl, t-butyl, benzyl or 4-methoxybenzyl ester of glycine (R"=H), alanine (R"=Me), valine (R"=iso-Pr), leucine (R"=iso-Bu), isoleucine (R'=sec-Bu), cyclopropylalanine (R"=CH₂cycPr), cyclobutylalanine (R"=CH₂cycBu), cyclohexylglycine (R"= cycHex) or a N-alkyl amino-acid, such as N-methyl glycine (R'=Me), or a cyclic amino-acid, such as proline (R'R"=— (CH₂)₃—), with 1-4 using sodium triacetoxyborohydride or sodium cyanoborohydride in a suitable solvent such as methylene chloride, DCE, THF, acetonitrile or methanol affords 1-5. Final deprotection of the ester under conditions to which the R''' group is stable, such as HCl in ether, TFA or formic acid for t-butyl and 4-methoxybenzyl esters, hydrogenation for benzyl esters or standard hydrolysis for alkyl or benzyl esters, affords the final product(s) 1-6 which is the N-cyclopentyl HIV CCR5 antagonist compound of interest. The two individual C-1 isomers (four diastereomers when either the cyclopentyl scaffold or the amino-acid are racemic) can be separated by flash chromatography, Prep TLC or HPLC methods as either the penultimate esters 1-5 and/or the final compounds 1-6.

SCHEME 2

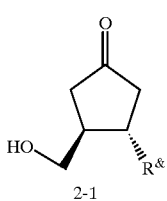

2-1

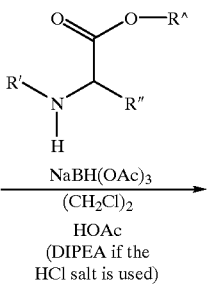

NaBH(OAc)₃
(CH₂Cl)₂
HOAc
(DIPEA if the HCl salt is used)

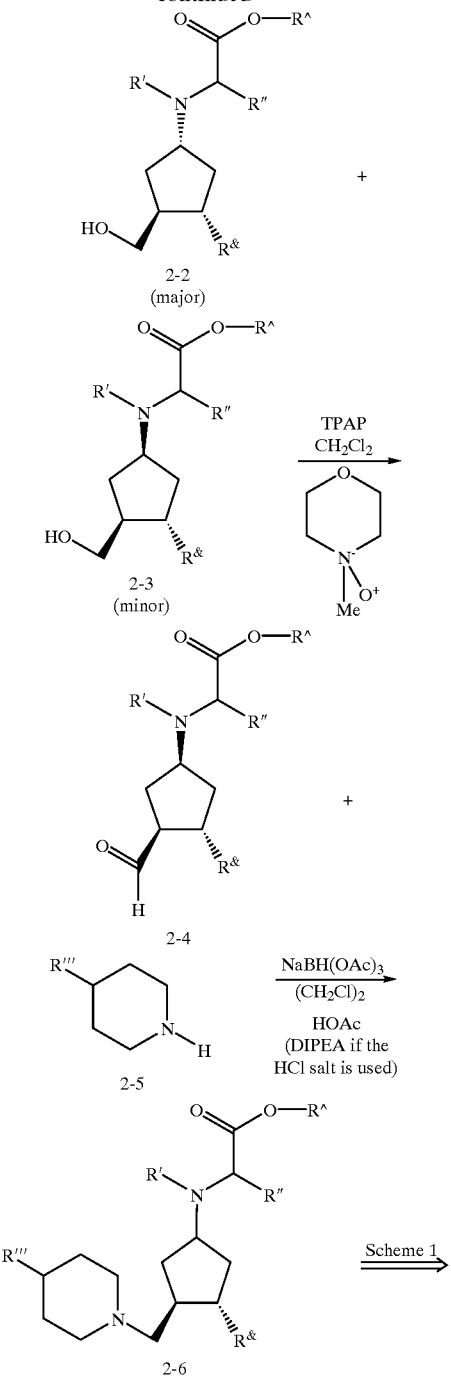

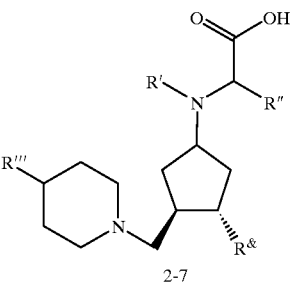

2-7

An alternative route for the preparation of some 1,3,4-trisubstituted cyclopentanes useful as CCR5 antagonists is given in Scheme 2. Reductive alkylation with ketone alcohol 2-1 (Scheme 1) of a variety of amino-acid esters (See Scheme 1) affords the alcohols 2-2 and 2-3, of which 2-2 is the major product (lower $R_f$ when R" is (S), higher $R_f$ when R" is (R)) and 2-3 is the minor product (higher $R_f$ when R" is (S), lower $R_f$ when R" is (R)). Separation of the individual diastereomers (2 when both reactants are non-racemic, 4 when only one is non-racemic) can be done at this intermediate or at a later step. Oxidation of 2-2 and/or 2-3 to the aldehyde(s) 2-4 can be done as described in Scheme 1, preferably now with N-methylmorpholine-N-oxide/TPAP due to the presence of the secondary N-H. Reductive alkylation of a 4-substituted piperidine 2-5 with the aldehyde of 2-4, using for example sodium triacetoxyborohydride or sodium cyanoborohydride in a suitable solvent such as methylene chloride, 1,2-dichloroethane, THF, acetonitrile or methanol, then provides the 3-((4-substituted piperidin-1-yl)methyl)cyclopentane derivative 2-6. The intermediate ester(s) 2-6 can then be converted to the final product(s) 2-7 as described in Scheme 1.

SCHEME 2A

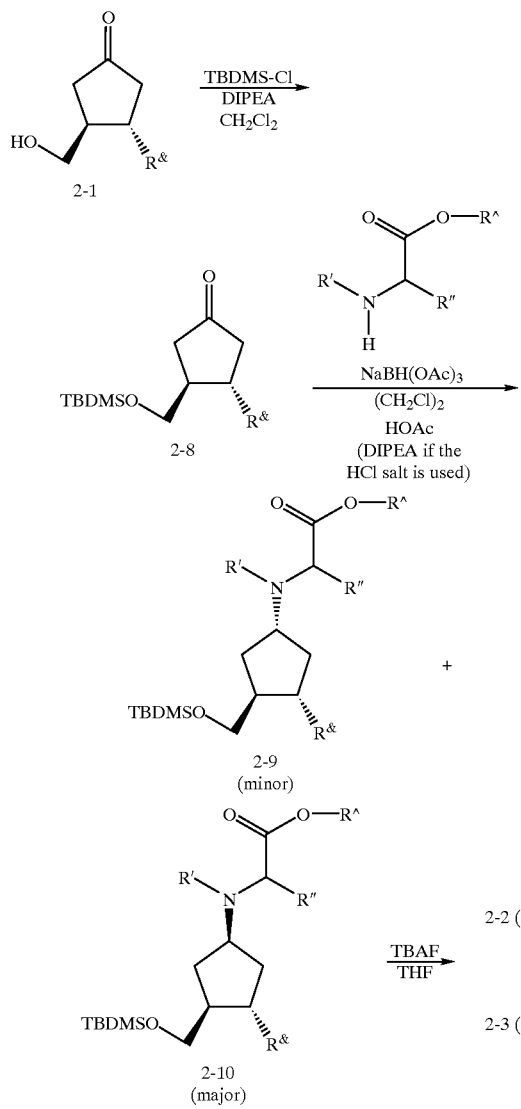

An alternative preparation of the intermediates 2-2 and 2-3 in Scheme 2 which reverses the C-1 isomeric selectivity is shown in Scheme 2A. Silylation of the alcohol moiety of 2-1 gives the silyl ether 2-8. Reductive alkylation of the aforementioned amino-acid esters now using the silyl ether 2-8 affords the products 2-9 and 2-10 in an essentially opposite ratio as is obtained in Scheme 2 for 2-2 and 2-3. TBAF desilylation then affords primarily 2-3. Thus, the preferred C-1 orientation can be selected for depending on the requirements of the desired final compounds.

SCHEME 2B

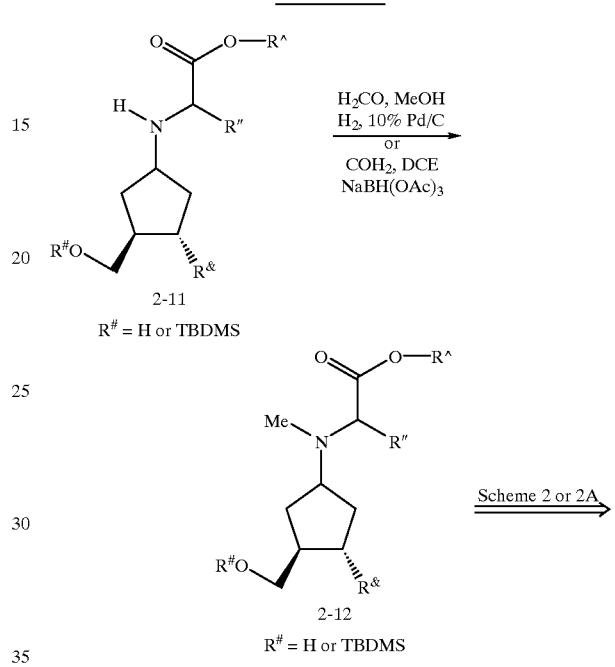

An alternative preparation of the intermediates 2-2 or 2-3 in Scheme 2 and intermediates 2-9 and 2-10 in Scheme 2A when R' is Me is shown in Scheme 2B. When 2-11 is formed in the reductive amination with ketones 2-1 ($R^\#$=H) or 2-8 (R#=TBDMS), a second reductive amination of 2-11 with formaldehyde, either in the presence of hydrogen and a suitable catalyst, such as 10% Pd/C or Pearlman's catalyst, in methanol or standard reaction with sodium triacetoxyborohydride in 1,2-dichloroehthane, affords the methylated intermediates 2-12. These intermediates can be further elaborated to the final products as described in Scheme 2 and/or 2A.

SCHEME 3

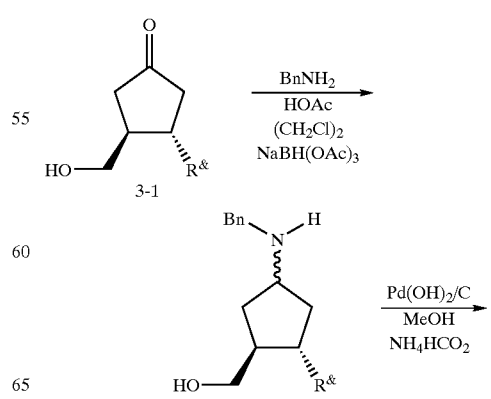

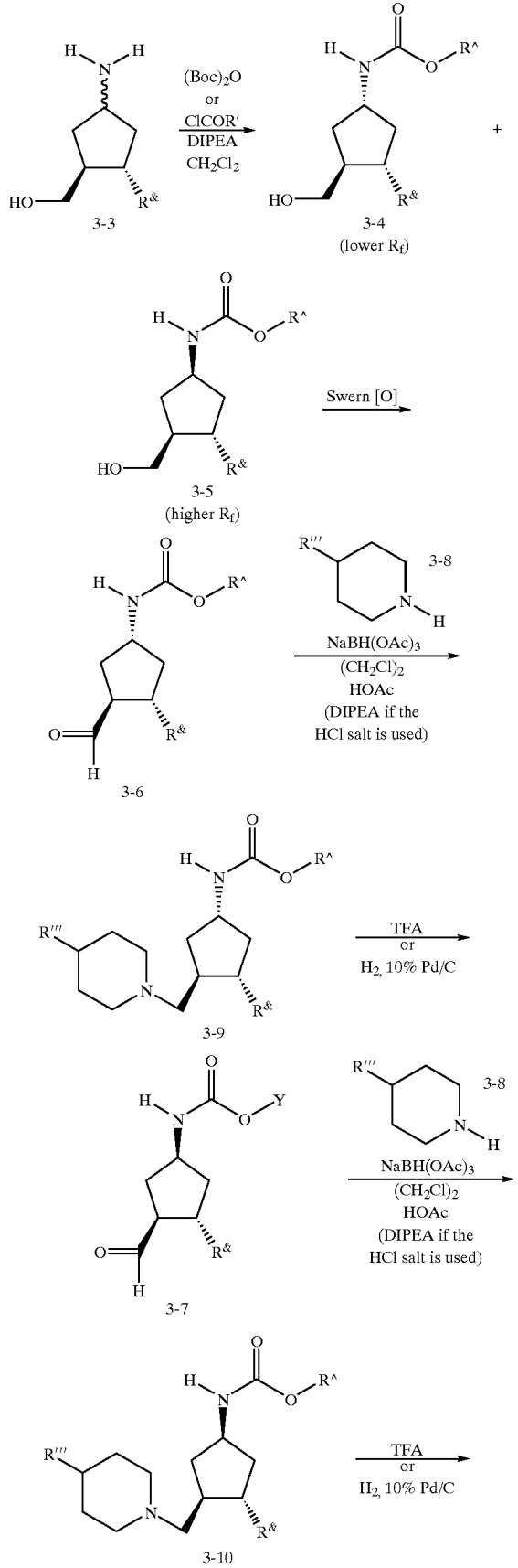
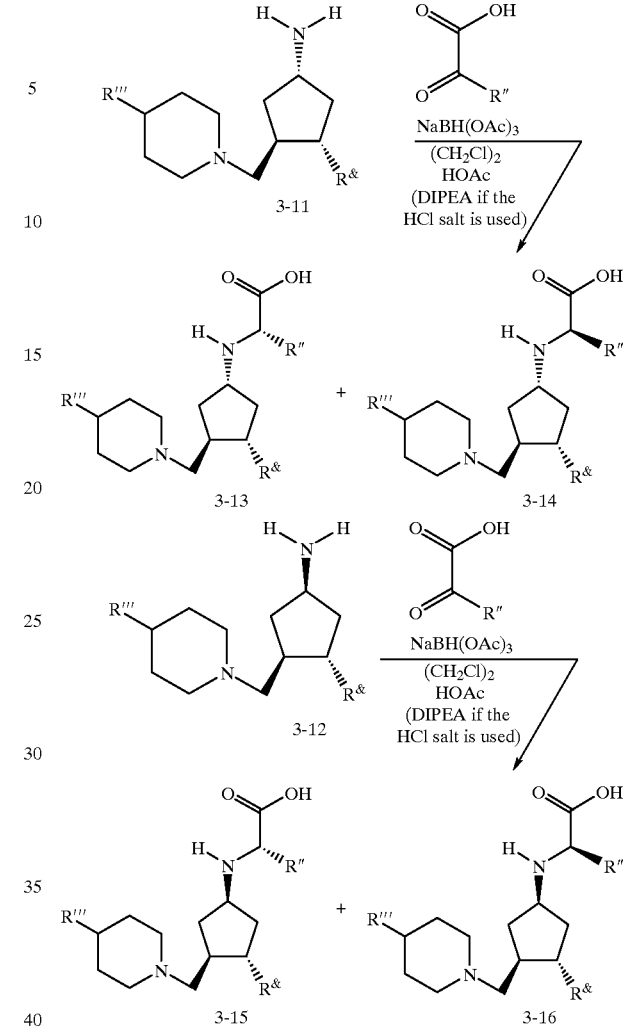

An alternative route for the preparation of some 1,3,4-trisubstituted cyclopentanes useful as CCR5 antagonists is given in Scheme 3. Reductive alkylation of benzylamine with ketone-alcohol 3-1 (Scheme 1, either racemic or non-racemic), using for example sodium triacetoxyborohydride or sodium cyanoborohydride, gives 3-2 which can be hydrogenated under standard conditions in methanol in the presence of a palladium catalyst, for example Pd/C or Pearlman's catalyst and using either hydrogen under pressure or ammonium formate at reflux, to afford the primary amine 3-3. Reaction of the amine with CBZ chloride or Boc anhydride gives the amine protected carbamates 3-4 and 3-5 as a mixture of C-1 isomers which can be separated. Oxidation to the aldehydes 3-6 and 3-7 is carried out under Swern conditions or with N-methylmorpholine/TPAP. The relative stereochemistry of the C-1 to the C-3 and C-4 substituents was determined by NMR Noe experiments on either the alcohols 3-4 and 3-5 or the aldehydes 3-6 and 3-7. Reductive alkylation of a 4-substituted piperidine 3-8 with the individual aldehydes 3-6 and 3-7, using for example sodium triacetoxyborohydride or sodium cyanoborohydride in a suitable solvent such as methylene chloride, 1,2-dichloroethane, THF, acetonitrile or methanol, then provides each of the C-1 amino-protected isomeric 3-((4-substitutedpiperidin-1-yl)methyl)cyclopentane derivatives 3-9 and 3-10. Deprotection of the C-1 amino with either TFA (for R^=t-butyl) or standard hydrogenation (for R^=Bn) depending on the stability of the piperidine R''' group affords the amines 3-11 and 3-12. These amines can then be individually reductively alkylated as above with 2-oxo-acetic acids, such as 2-oxovaleric (R"=n-Pr), 4-methyl-2-oxovaleric (R"=iso-Bu), 2-oxophenylacetic (R"=Ph), to afford the final compounds 3-13 and 3-14 and 3-15 and 3-16 as mixtures of the R" isomers. In the case of R"=iso-Bu and non-racemic cyclopentyl scaffold, comparison of the HPLC of these products with those obtained in Scheme 2 allowed the stereochemical assignments of all the final products and intermediates.

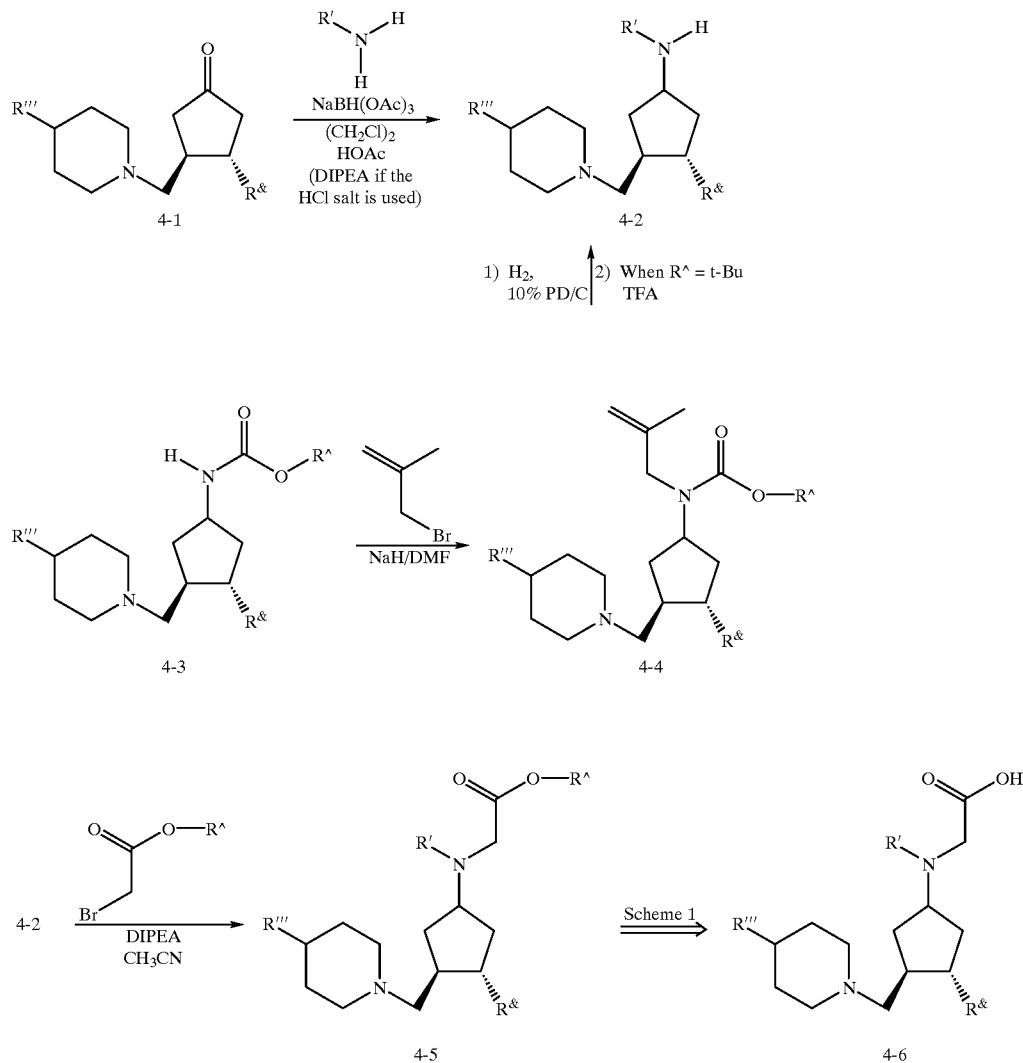

An alternative route for the preparation of some 1,3,4-trisubstituted cyclopentanes useful as CCR5 antagonists is given in Scheme 4. Reductive alkylation, using for example sodium triacetoxyborohydride or sodium cyanoborohydride, of an alkyl amine with the ketone 4-1 (Scheme 1) gives 4-2 as a mixture of C-1 isomers which may be separated. Alternatively, carbamate 4-3 (see Scheme 3) can be alkylated with an alkyl or allyl halide, such as 1-bromo-2-methylprop-2-ene, and a strong base, such as sodium hydride in DMF, followed by hydrogenation under standard conditions to reduce the allyl. When R^ is Bn, removal of the CBZ can occur simultaneously to give the same amine intermediate 4-2. When R^ is t-butyl, a subsequent reaction with TFA is required to give 4-2. Alkylation of the amine with t-butyl or benzyl bromoacetate affords 4-5 which can be converted to the desired final compound(s) 4-6 as described in Scheme 1.

SCHEME 5

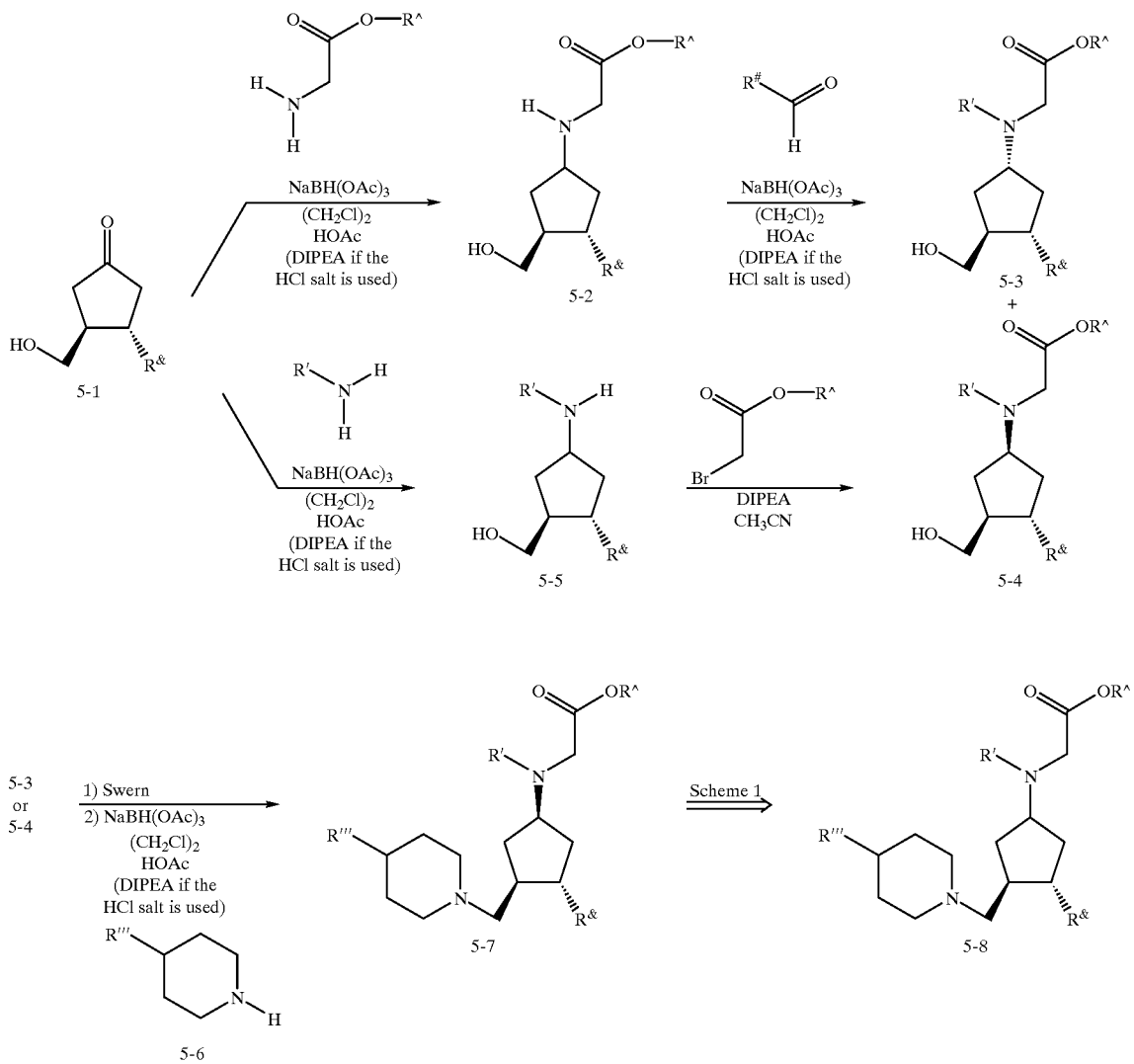

An alternative route for the preparation of some 1,3,4-trisubstituted cyclopentanes useful as CCR5 antagonists is given in Scheme 5. Reductive alkylation, using for example sodium triacetoxyborohydride or sodium cyanoborohydride, of glycine t-butyl, benzyl or PMB ester with the ketone-alcohol 5-1 (Scheme 1) gives 5-2 as a mixture of C-1 isomers. A second reductive alkylation with a ketone or aldehyde affords the N-alkyl glycine derivatives 5-3 and 5-4 which can be separated chromatographically either before and/or after the second alkylation. Also, the order of the steps can be reversed such that reductive alkylation of an amine with 5-1 first to give 5-5, followed by alkylation with an alkyl or benzyl bromoacetate as in Scheme 4, affords 5-3 and 5-4. These reactions generally give 5-3 as the predominate product. Individual oxidation of the alcohols 5-3 and 5-4 can be done either under Swern conditions or using the N-methylmorpholine/TPAP method to give the aldehyde intermediate(s) followed by a second or third reductive alkylation of a 4-substituted piperidine 5-6, using for example sodium triacetoxyborohydride or sodium cyanoborohydride in a suitable solvent such as methylene chloride, 1,2-dichloroethane, THF, acetonitrile or methanol, which then provides the 3-((4-substitutedpiperidin-1-yl)methyl)cyclopentane derivative 5-7. This intermediate can then be converted to the final product(s) 5-8 as described in Scheme 1.

SCHEME 5A

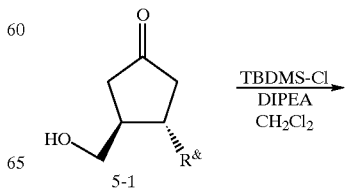

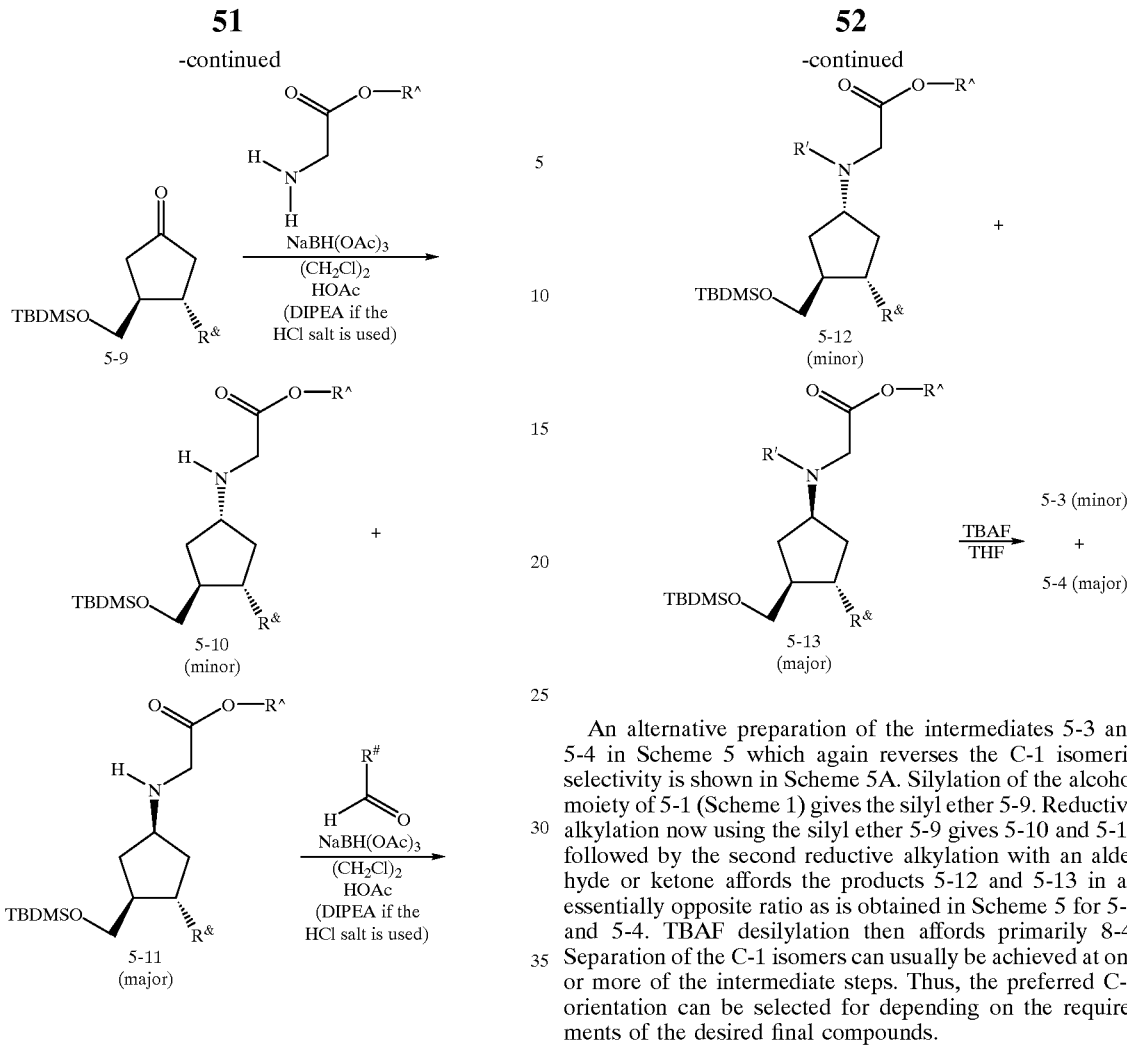

An alternative preparation of the intermediates 5-3 and 5-4 in Scheme 5 which again reverses the C-1 isomeric selectivity is shown in Scheme 5A. Silylation of the alcohol moiety of 5-1 (Scheme 1) gives the silyl ether 5-9. Reductive alkylation now using the silyl ether 5-9 gives 5-10 and 5-11 followed by the second reductive alkylation with an aldehyde or ketone affords the products 5-12 and 5-13 in an essentially opposite ratio as is obtained in Scheme 5 for 5-3 and 5-4. TBAF desilylation then affords primarily 8-4. Separation of the C-1 isomers can usually be achieved at one or more of the intermediate steps. Thus, the preferred C-1 orientation can be selected for depending on the requirements of the desired final compounds.

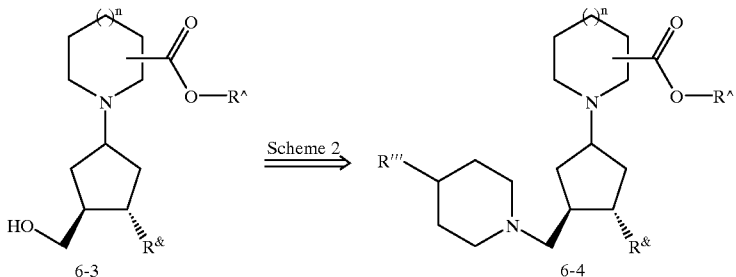

An alternative route for the preparation of some 1,3,4-trisubstituted cyclopentanes useful as CCR5 antagonists is given in Scheme 6. Reductive alkylation, using for example sodium triacetoxyborohydride or sodium cyanoborohydride, of a cyclic secondary amino-acid 6-1, such as D- or L-proline t-butyl ester (n=0), β-proline t-butyl ester (n=0), 2-, 3-, and 4-t-butylcarboxypiperidine (n=1), with the ketone-alcohol 5-2 (Scheme 1) gives 5-3 and 5-4 as a mixture of C-1 isomers which may be separated. These intermediates can then be converted to the final product(s) as described in Scheme 2.

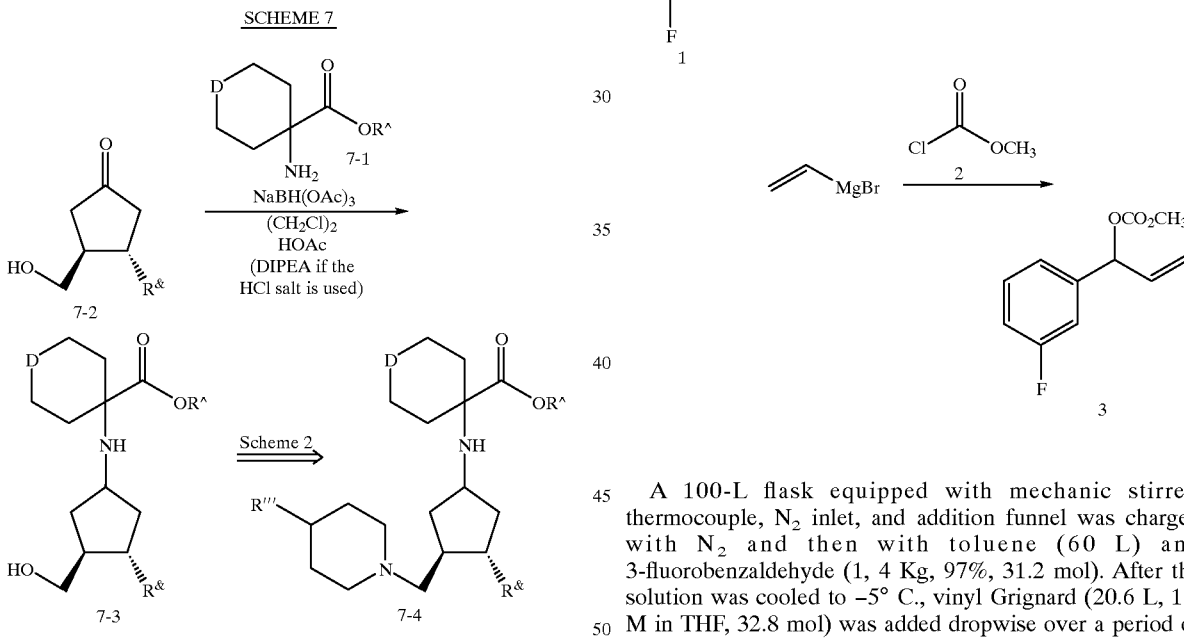

An alternative route for the preparation of some 1,3,4-trisubstituted cyclopentanes useful as CCR5 antagonists is given in Scheme 7. Reductive alkylation, using for example sodium triacetoxyborohydride or sodium cyanoborohydride, of a cycloalkyl amino-acid 7-1, such as 1-aminocyclopentane carboxylic acid t-butyl ester (D=single bond) or a heterocyclic amino-acid, such as 4-aminomorpholin-2-yl carboxylic acid t-butyl ester (D=O) with the ketone-alcohol 7-2 (Scheme 1) gives 7-3 and 7-4 as a mixture of C-1 isomers which may be separated. These intermediates can then be converted to the final product(s) as described in Scheme 2.

Further description of the preparation of N-cyclopentyl compounds useful as CCR5 antagonists starting with the hydroxymethylcyclopentanone compounds of Formula (XII) is provided in WO 00/76972.

The following examples serve only to illustrate the invention and its practice. The examples are not to be construed as limitations on the scope or spirit of the invention.

EXAMPLE 1

Allyl Carbonate Formation

A 100-L flask equipped with mechanic stirrer, thermocouple, $N_2$ inlet, and addition funnel was charged with $N_2$ and then with toluene (60 L) and 3-fluorobenzaldehyde (1, 4 Kg, 97%, 31.2 mol). After the solution was cooled to −5° C., vinyl Grignard (20.6 L, 1.6 M in THF, 32.8 mol) was added dropwise over a period of 1.5 hours while maintaining the temperature below 0° C. The reaction was stirred for an additional 60 minutes at −5 to 0° C., at which point HPLC assay indicated ~0.4 area % of starting material vs. product. Methyl chloroformate (2, 2.74 L, d=1.223, 35.4 mol) was added via an addition funnel over 30 min while maintaining the temperature below 0° C. After stirring for 60 min, 0.5 N HCl (40 L) was added, while maintaining the temperature <20° C. The organic layer was separated, and filtered through silica gel (4 Kg). The filtrates containing the product was concentrated to remove solvents. The weight of the concentrated material was 8.88 Kg. $^1$H NMR of the solution showed the material was 56.7 wt %, yielding 5.01 Kg of allyl carbonate 3 as a light yellow oil.

$^1$H-NMR(400 MHz, $CDCl_3$) δ 7.34 (q, 1H), 7.16 (d, 1H), 7.09 (d, 1H), 7.02 (m, 1H), 6.02 (m, 2H), 5.36 (m,2H), 3.85 (s, 3H). $^{13}$C-NMR (400 MHz, $CDCl_3$) δ 164.1, 161.6, 154.9, 140.8, 135.2, 103.2, 122.5, 118.1, 114.6 (dd), 79.3, 54.9.

EXAMPLE 2

Asymmetric Alkylation
Part A: Sodium dimethyl malonate

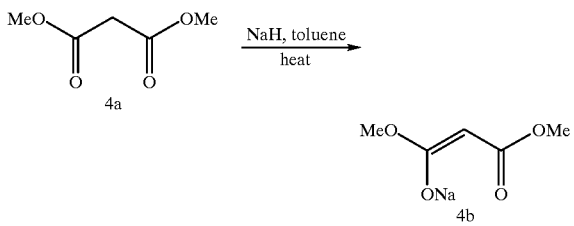

A 100 L round bottom flask was charged with dimethyl malonate (4a, 4.25 kg, 31.52 mol) and toluene (50 L), and was then flushed with nitrogen followed by the addition of sodium hydride (60% dispersion in mineral oil, 1.197 Kg, 29.94 mol) in roughly four equal portions over 20 minutes. The resulting mixture was heated at 70° C. for 45 minutes and then cooled to 5° C. The thick slurry was filtered and flushed with heptane to give the product 4b as a white fluffy solid (6.063 Kg, 81% pure, remainder toluene, quantitative yield).

Part B: Ligand

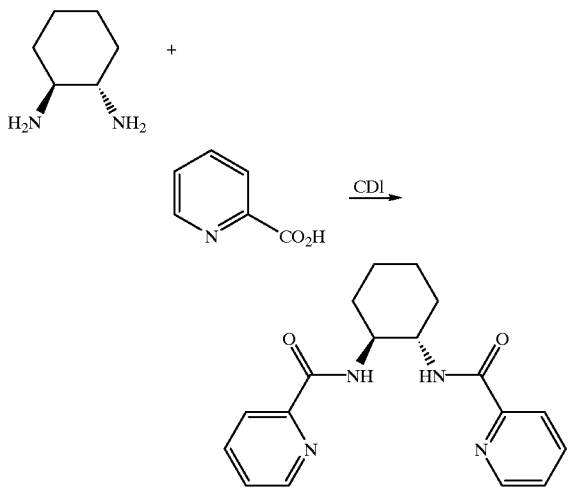

A 22 L flask was charged with 1,1'-carbonyldiimidazole (1.7 Kg, 10.48 mol) and THF (7.5 L). Solid picolinic acid (1.36 Kg, 11 mol) was added to the slurry at room temperature. The reaction was endothermic causing the mixture to cool from 18° C. to 12° C. The reaction mixture was then warmed to 18–19° C. The resulting clear solution was stirred for 1 h and molten (1S, 2S)-(+)-1,2-diaminocyclohexane (0.5 Kg, 4.38 mol) was added over one hour while keeping the temperature below 50° C. The beaker and funnel were rinsed with 2.5 L of THF. The reaction was stirred at room temperature for 15 h. Water (0.5 L) was added to the thin slurry giving a clear solution and the reaction mixture was stirred for 1 h. The reaction mixture was concentrated to an orange semi-solid by rotary evaporation. The reaction product was slurried in 5 L of ethanol and concentrated by rotary evaporation. The reaction product was dissolved in ethanol (5 L) at 64–65° C. The solution was allowed to cool. The solution turned hazy around 58° C. At this temperature, the hazy solution was seeded (10 g) and cooled to −8° C. The resulting white crystals were isolated by filtration on a sintered glass funnel, washed with 5 L of cold ethanol (−8 to −10° C.), dired under house vacuum with nitrogen sweep, and then dried in a vacuum oven (35° C.). This resulted in the isolation of 1.23 Kg (86.3%) of white crystalline solid.

$^1$H NMR (400 mHz, CDCl$_3$) δ 8.50–8.49 (m, 2H), 8.23 (d, J=6.47 Hz, 2H), 8.02–7.99 (m, 2H), 7.69–7.64 (m, 2H), 7.29–7.24 (m, 2H), 4.03 (bs, 2H), 2.18–2.15 (m, 2H), 1.79 (bs, 2H), 1.42–1.41 (m, 4H)

$^{13}$C NMR (CDCl$_3$) δ 164.5, 149.8, 148.1, 136.9, 125.8, 122.0, 53.2, 32.6, 24.8

Part C: Alkylation

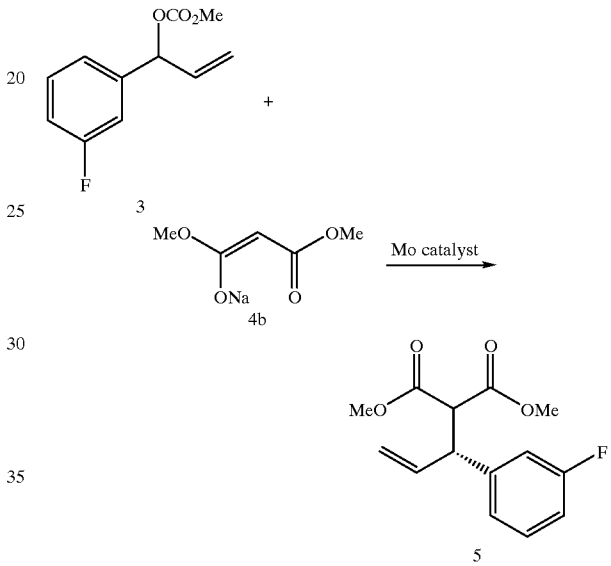

A 2 L round bottom flask equipped with a mechanical stirrer, vacuum inlet, argon inlet and a septa was charged with Mo(CO)$_6$ (218.8 g, 0.828 mol; 0.1 eq.) and ligand (402 g, 1.242 mol; 0.15 eq.), and then evacuated and back filled with argon (3 cycles). To this mixture was added toluene (4.36 L) and the resulting solution was evacuated and back filled with argon (3 cycles). The solution was heated to 85° C. for 4.0 hr. Separately, a 50 L flask was charged with sodium dimethyl malonate 4b (2.36 kg; 1.5 eq) and toluene (30.6 L). The heterogeneous solution was heated to 50–55° C. followed by the addition of the carbonate 3 (87.1%; 2 kg; 8.28 mol; 1 eq.) in toluene (3 L) and the molybdenum/ligand solution. The mixture was heated at 85° C. for 15 h, and then cooled to 25–30° C. Water (20 L) was added to the mixture, and the resulting mixture was transferred to an extractor. The organic layer was separated, concentrated to approximately 5 L, filtered through SiO2, concentrated under vacuum, to afford an oil containing 2.077 Kg (94.3% yield, ee=96.1%) of the desired product. Ratio of regioisomers was 19:1 trans to cis. $^1$H-NMR (400MHz, CDCl3) δ 7.28 (m, 1H), 7.02 (d, 1H, J=7.8 Hz), 6.95(m, 2H), 6.71 (m, 1H), 5.14 (dd, 2H), 4.12 (t, 1H, J=8.3 Hz)), 3.85 (d, 1H, J=11.0 Hz), 3.76 (s, 3H), 3.54 (s, 3H); $^{13}$C-NMR (400 MHz, CDCl$_3$) δ167.9, 167.6, 164.0, 161.6, 142.6, 137.1, 130.1, 123.6, 117.2, 114.9(d), 114.1 (d), 57.1, 52.6, 49.3

EXAMPLE 3

Saponification/Decarboxylation

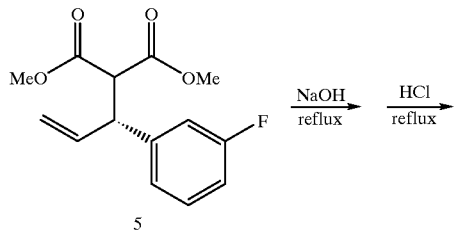

5

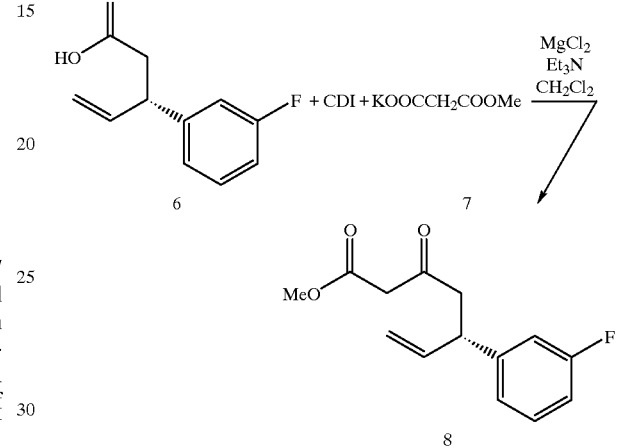

A solution of malonic ester intermediate 5 (2.256 kg, 8.47 mol; 36.1% by wt in MTBE, total wt 6.251 kg) was charged to a 50 L, 4-necked round bottom flask, equipped with mechanical stirrer, stopper, thermocouple, and batch concentrator. The solution was concentrated at 29" vacuum until no more distillate was obtained at an internal temperature of 15° C. To the orange oil was added water (11 L) and 5 N NaOH (5 L), and the resulting mixture was refluxed for 30 min. The mixture was allowed to cool to 18–23° C. and the volatiles were removed by distillation at atmospheric pressure. The distillation was stopped when the level of MeOH reached 3 mole percent. A total of 6.7 L of distillate was collected. The pH of the aqueous phase was adjusted to 0.81 using conc. HCl (1.9 L). The mixture was refluxed for 12 h. The reaction mixture was cooled to 46° C. and extracted twice with toluene (once with 5.5 L and once with 3.5 L). The toluene extracts were combined and extracted once with 5% NaCl (aq) (3 L). The toluene solution was dried with $Na_2SO_4$ (1 kg) and filtered. The solution was assayed by HPLC. The yield was 1.429 kg (86.9%). $^1$H NMR ($CDCl_3$) δ 2.77 (m, 2H), 3.87 (m, 1H), 5.12 (m, 2H), 5.96 (m, 1H), 6.93 (m, 2H), 7.01 (m, 1H), 7.28

A 72 L, 4-necked flask, equipped with mechanical stirrer, thermocouple, reflux condenser with $N_2$ inlet, addition funnel, and steam pot, was charged with a toluene solution of the monoacid 6 (10.6 kg of solution, 1.3 kg of monoacid, 6.69 mol). To the solution was added acetonitrile (29.3 L), and the resulting mixture was heated to reflux. When the solution began to reflux (about 78° C.), (S)-α-methylbenzylamine (779 g) was added over 5 min. The solution was allowed to cool. At 64° C., the salt began to crystallize. At 58° C., ice bath cooling was applied. The temperature dropped to 10° C., and the mixture was stirred at that temperature for 45 min. The mixture was filtered, and the cake was washed with an ice-cold 3:1 mixture of acetonitrile and toluene (9 L). The monoacid salt wet cake was placed under positive $N_2$ pressure using a plastic bag over the filter pot.

A 50 L extractor was charged with the monoacid salt wet cake (13.91 moles). To the extractor were added water (20 L), 50% NaOH (820 mL), and $CH_2Cl_2$ (12 L). The contents were mixed thoroughly, allowed to settle, and the layers were separated. The aqueous phase was extracted again with $CH_2Cl_2$ (12 L). To the aqueous phase was added toluene (19 L) and conc. HCl (1.5 L). The layers were separated, and the aqueous phase was extracted again with toluene (4 L). The toluene extracts were combined and extracted with 5% NaCl solution (10 L). The toluene layer was dried with $Na_2SO_4$ (1 kg). The mixture was filtered, the cake was washed with toluene (2 L), and the combined filtrate and wash was assayed by HPLC. The yield was 2522 g (93.4% overall for salt formation and salt break).

EXAMPLE 4

Chain Extension

The toluene solution from Example 3 (11230 g of a solution containing 1158 g of acid and 1043 g of a second solution containing 102 g of acid) was concentrated to an oil using a Buchi rotavapor. The oil was dissolved in $CH_2Cl_2$ (0.5 L). The KF was 36 μg/mL. A 50 L, 4-necked round bottom flask, equipped with mechanical stirrer, thermocouple, reflux condenser with $N_2$ inlet, addition funnel, and steam pot, was charged sequentially with $CH_2Cl_2$ (5.5 L), monomethylmalonate potassium salt (7, 1.52 kg), and magnesium chloride (618 g). The mixture was cooled to 0–5° C. Triethylamine (2.71 L) was charged to the addition funnel and added to the mixture over 2–5 min. The addition was slightly exothermic; the temperature rose 2° C. The mixture was aged for 30 min at 0–5° C., then warmed to 20° C. and aged for 30 min. A 22 L, 4-necked round bottom flask, equipped with mechanical stirrer, thermocouple, $N_2$ inlet, dry ice condenser, and addition funnel, was charged with $CH_2Cl_2$ (4 L) and 1,1'-carbonyldiimidazole (1.10 kg). The monoacid solution from above was charged to the addition funnel and added to the 22 L flask over 30–40 min to give a solution. Gas ($CO_2$) vigorously evolved, which entrained $CH_2Cl_2$, hence the need for the dry ice condenser. The resulting solution of activated monoacid was pumped into the 50 L flask. The dry ice condenser was moved from the 22 L flask to the top of the water condenser on the 50 L flask. The reaction mixture was heated to 41° C. During the addition of activated monoacid, the temperature rose from 20.1° C. to 20.7° C. The temperature continued to slowly rise to 28° C., at which point steam was intermittently applied to the 50 L flask. The progress of the reaction was followed by HPLC. When the reaction was complete (about 1.5 h), the mixture was cooled to 0–5° C. To the cold mixture was added cold 2 N HCl (19 L). The pH of the aqueous phase was 2.9. The addition was exothermic; the temperature increased to 20° C. The two phase mixture was transferred to a 50 L extractor, and the layers were separated. The aqueous phase was extracted with $CH_2Cl_2$ (3 L). The $CH_2Cl_2$ extracts were combined and dried with anhydrous $Na2SO_4$ (1 kg). The mixture was filtered and the cake was washed with $CH_2Cl_2$ (1 L). The filtrate and washes were combined. Final yield was >95%.

$^1$H NMR ($CD_3Cl$) δ 2.98 (m, 2H), 3.39 (d, J=1.2 Hz, 2H), 3.70 (s, 3H), 3.94 (m, 1H), 5.06 (m, 2H), 5.93, (m, 1H), 6.90 (m, 1H), 6.92 (m, 1H), 6.99 (m, 1H), 7.26 (m, 1H). $^{13}$C NMR ($CD_3Cl$) δ 43.6, 47.8, 49.3, 52.2, 113.5 (d, J=20.9 Hz), 114.4 (d, J=21.7 Hz), 115.3, 123.3 (d, J=3.2 Hz), 130.0 (d, J=8.0 Hz), 139.5, 145.0 (d, J=7.2 Hz), 162.8 (d, J=Hz), 167.2, 200.2.

EXAMPLE 5

Diazo Transfer

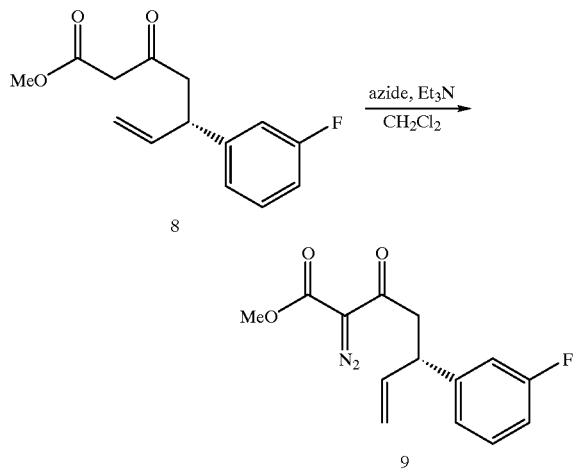

A 50 L, 4-necked round bottom flask, equipped with mechanical stirrer, thermocouple, addition funnel, $N_2$ inlet, and steam pot, was charged with a solution of ketoester intermediate 8 (8823 g of solution, 1300 g of ketoester in 1,2-dichloroethane). Additional 1,2-dichloroethane (7 L) was charged to the flask, followed by 4-acetamidobenzenesulfonyl azide (1.25 kg). The solution was heated from about 18° C. to 21° C. with steam. (Note: the dissolution of azide was endothermic.) Triethylamine (2.17 L) was added over 40 min with water bath cooling to maintain a temperature of 19–23° C. The reaction was stirred at 18–23° C. for approximately 9 h. The reaction was mildly exothermic. The reagent product, 4-acetamidobenzenesulfonyl amide, began to precipitate from the reaction during the addition of triethylamine and eventually formed a thick slurry. The reaction was followed by HPLC and was judged complete when the amount of starting material was <0.5%. When completed, the reaction mixture was filtered, and the cake was washed four times with 1,2-dichloroethane (3×2 L displacement washes, 1×1 L slurry wash). The filtrate and washes were combined and extracted with cold (5–10 C) 2N HCl (7.4 L). The extraction was exothermic and was done in a 50 L extractor with cooling to maintain a temperature of 20–22° C. The pH of the aqueous phase was 1.0. The organic layer was extracted twice with water (2×7 L). The organic extract was charged to a 50 L, 4-necked round bottom flask, equipped with mechanical stirrer, thermocouple, $N_2$ inlet, and stopper. The solution was dried for 4 h with $Na_2SO_4$ (1 kg). The organic solution was passed through a 5 μ inline filter. The final weight of organic solution was 25.6 kg. Final yield of 9 was >95%.

$^1$H NMR ($CDCl_3$) δ 3.32 (d, J=7.6 Hz, 2H), 3.84 (s, 3H), 4.02 (m, 1H), 5.08 (m, 2H), 5.97 (m, 1H), 6.90 (m, 1H), 6.96 (m, 1H), 7.04 (m, 1H), 7.26 (m, 1H).

EXAMPLE 6

Cyclopropanation

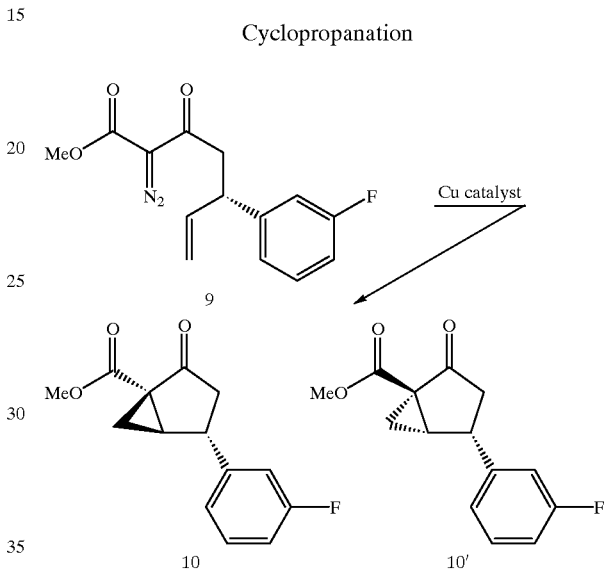

100 L flask equipped with a 5 L addition funnel, reflux condenser, temperature probe, stopper, and air-driven overhead stirrer was charged with 1,2-dichloroethane (11 L) and $(CH_3CN)_4CuPF_6$ (55.41 g, 0.149 mol). The temperature-controlled waterbath was set to 77° C., and the starting diazo substrate 9 (1373 g in DCE solution, 4.97 mol) was added to the reaction vessel over a period of 8 hours, with the reaction temperature maintaining at 77–81° C. After finishing addition, reaction was stirred for 1 additional hour, steam was turned off, and ice was added to the waterbath. After cooling for 2 hours the flask contents were pumped into a 100 L extractor, and the reaction flask was rinsed with 2 L $CH_2Cl_2$. Brine (30 L) was pumped into the extractor and the mixture stirred for 10 minutes, then settled for 30 minutes. The layers were separated and the organics were dried over $MgSO_4$ in a cold room overnight. The mixture was filtered and the organics were concentrated, yielding 96.5% of the trans and cis mixture 10 and 10', 77.5% of trans only (4.47:1 trans:cis).

$^1$H-NMR (400 MHz, $CDCl_3$) δ7.31 (m, 2H), 6.95 (m, 2H), 3.82 (s, 3H), 3.49 (d, 1H, J=8.5 Hz), 2.76 (m, 1H), 2.64(dd, 1H, J=8.2 Hz), 2.28 (d, 1H, J=19.1 Hz), 2.15 (m, 1H),1.54 (t, 1H, J=5.3 Hz). $^{13}$C-NMR (400 MHz, $CDCl_3$) δ 205.4, 168.3, 163.1 (d, J=2.4 Hz), 147.1, 130.8, 122.0, 114.1(d), 113.6(d), 52.6, 42.4, 39.1, 39.0, 38.0, 21.5.

EXAMPLE 7

(+)-trans-3-Hydroxymethyl-4-(3-fluorophenyl)cylopentanone (12)

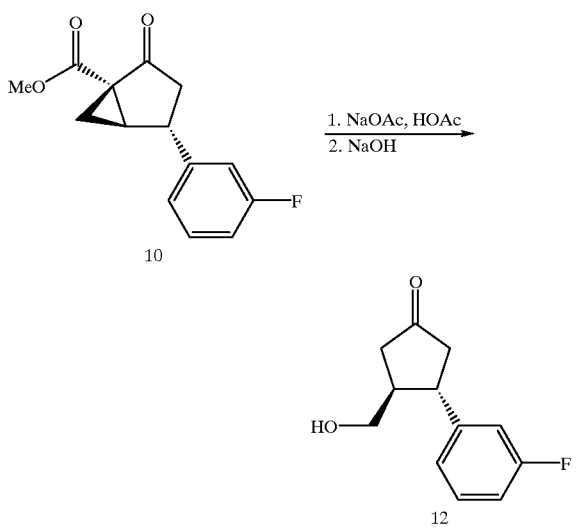

A 72 L round bottom flask equipped with a temperature probe, overhead stirrer, nitrogen and vacuum inlet was charged with the cis/trans cyclopropane mixture prepared as described in Example 6 (6.45 Kg of trans starting material, 3.4 mol), NaOAc (2.77 Kg, 33.8 mol), and HOAc (14 L, 244 mol). The mixture was evacuated and back filled with $N_2$ (3 cycles) and heated to 105° C. for 15 h followed by distillation of 12–13 L of acetic acid. The mixture is cooled to 50° C. followed by the addition of DMF (15 L). To the solution was added 3N NaOH until pH=>12 (keeping solution temp <35° C.) followed by heating to 70° C. for 30 min. The solution was cooled to room temperature and transferred into an extractor. To the extractor was added 30 L of MTBE, and the aqueous layer separated and back extracted with 30 L of MTBE. The organic layers were combined, washed with 30 L of 10% NaCl in water, dried over $MgSO_4$, filtered, and concentrated to yield 2.23 Kg of material containing 698 g of product 12 (98% yield) with the remainder MTBE.

$^1$H NMR ($CDCl_3$) δ 2.3–2.45 (m, 2H), 2.5 (m, 1H), 2.61 and 2.77 (dABq, 2H), 2,28 (ddd, 1H), 3.61 and 3.75 (dABq, 2H), 6.9–7.0 (m, 2H), 7.06 (d, 1H), 7.3–7.4 (m, 1H).

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a hydroxymethylcyclopentanone compound of Formula (XII):

(XII)

which comprises (Z4) reacting a mixture comprising a trans-bicyclo[3.1.0]hexane compound of Formula (X):

(X)

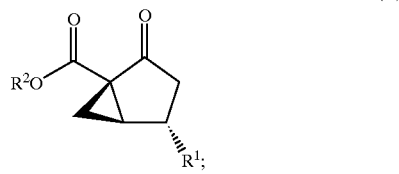

and a nucleophilic agent in solvent at a temperature in a range of from about 20 to about 200° C. to open the fused cyclopropyl ring of Compound X by addition of the nucleophile; and (Z5) contacting the reaction mixture of step Z4 with a base to form Compound XII;

wherein $R^1$ is phenyl, substituted phenyl, heterocycle, or substituted heterocycle, wherein each of the substituents on substituted phenyl or substituted heterocycle is independently selected from:
(a) halo,
(b) trifluoromethyl,
(c) hydroxy,
(d) $C_1$–$C_3$ alkyl,
(e) $C_1$–$C_3$ alkoxy,
(f) —$CO_2R^a$,
(g) —$NR^aR^b$, and
(h) —$CONR^aR^b$;

$R^2$ is $C_1$–$C_4$ alkyl, $C_1$–$C_4$ haloalkyl, or $C_2$–$C_6$ alkoxyalkyl;

each $R^a$ is independently hydrogen, $C_1$–$C_6$ alkyl, $C_1$–$C_6$ haloalkyl, $C_2$–$C_8$ alkoxyalkyl, $C_5$–$C_6$ cycloalkyl, benzyl, phenyl, substituted $C_5$–$C_6$ cycloalkyl, substituted benzyl or substituted phenyl, wherein each of the substituents on substituted $C_5$–$C_6$ cycloalkyl, substituted benzyl or substituted phenyl is independently selected from halo, nitro, $C_1$–$C_3$ alkyl, $C_1$–$C_3$ alkoxy and trifluoromethyl; and each $R^b$ is independently hydrogen, $C_1$–$C_6$ alkyl, $C_1$–$C_6$ haloalkyl, $C_2$–$C_8$ alkoxyalkyl, benzyl, phenyl, —$C_1$–$C_6$ alkyl-$C_3$–$C_6$ cycloalkyl, substituted benzyl, substituted phenyl, or substituted —$C_1$–$C_6$ alkyl-$C_3$–$C_6$ cycloalkyl, wherein each of the substituents on substituted benzyl, substituted phenyl, or substituted —$C_1$–$C_6$ alkyl—$C_3$–$C_6$ cycloalkyl is independently selected from halo, nitro, $C_1$–$C_3$ alkyl, $C_1$–$C_3$ alkoxy and trifluoromethyl.

2. The process according to claim 1, wherein the nucleophilic agent in step Z4 is selected from the group consisting of alkali metal salts of $C_1$–$C_6$ alkylcarboxylic acids, alkaline earth metal salts of $C_1$–$C_6$ alkylcarboxylic acids, $C_1$–$C_6$ thioalcohols, $C_1$–$C_6$ alkylamines, N-($C_1$–$C_4$ alkyl)-$C_1$–$C_6$ alkylamines, $C_5$–$C_7$ cycloalkylamines, $C_5$–$C_7$ azacycloalkanes, alkali metal $C_1$–$C_6$ alkoxides, alkali metal amides, and alkali metal cyanides.

3. The process according to claim 1, wherein the solvent employed in step Z4 is selected from the group consisting of $C_1$–$C_6$ alkylcarboxylic acids, dialkylformamides wherein each alkyl is independently a $C_1$–$C_4$ alkyl, dialkylacetamides wherein each alkyl is independently a $C_1$–$C_4$ alkyl, dialkyl ethers wherein each alkyl is independently a $C_1$–$C_6$ alkyl, $C_4$–$C_6$ cyclic ethers and diethers, $C_2$–$C_6$ aliphatic nitriles, N-methylpyrrolidone, and dimethylsulfoxide.

4. The process according to claim 1, wherein the reaction in step Z5 is conducted at a temperature in a range of from about 20 to about 110° C.

5. The process according to claim 1, wherein the base in step Z5 is selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl) ammonium hydroxides, and tri-($C_1$–$C_4$ alkyl)amines.

6. The process according to claim 1, wherein in step Z4 the nucleophilic agent is present in an amount of from about 0.7 to about 20 equivalents per equivalent of Compound X, and in step Z5 the base is present in an amount of from about 0.01 to about 20 equivalents per equivalent of Compound X.

7. The process according to claim 1, wherein reaction steps Z4 and Z5 are conducted in one pot.

8. The process according to claim 1, which further comprises recovering Compound XII.

9. The process according to claim 1, wherein $R^1$ is phenyl, substituted phenyl, thienyl, or substituted thienyl, wherein each of the substituents of substituted phenyl or substituted thienyl is independently selected from:
 (a) halo,
 (b) trifluoromethyl,
 (c) hydroxy,
 (d) $C_1$–$C_3$ alkyl, and
 (e) $C_1$–$C_3$ alkoxy.

10. The process according to claim 1, wherein $R^1$ is phenyl, substituted phenyl, or thienyl, wherein each of the substituents of substituted phenyl or substituted thienyl is independently selected from fluoro and chloro.

11. The process according to claim 1 for preparing a hydroxymethylcyclopentanone compound of Formula (XII):

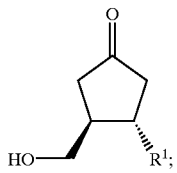

(XII)

which comprises:
 (Z4) reacting a mixture comprising a trans-bicyclo[3.1.0] hexane compound of Formula (X) and a cis-bicyclo[3.1.0]hexane compound of Formula (X'):

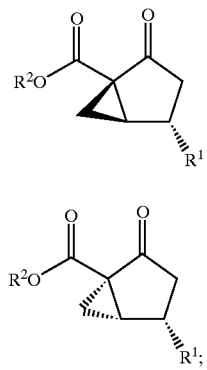

(X)

(X')

and a nucleophilic agent in solvent at a temperature in a range of from about 20 to about 200° C. to open the fused cyclopropyl ring of Compound X by addition of the nucleophile;

(Z5) contacting the reaction mixture of step Z4 with a base to form a mixture of Compound XII and a compound of Formula (XIII):

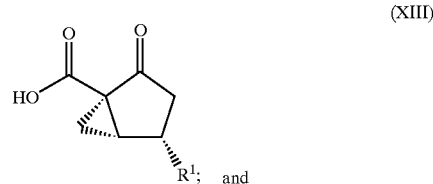

(XIII)

and (Z6) recovering Compound XII from the mixture.

12. The process according to claim 1, which further comprises
 (Z3) contacting a diazo compound of Formula (IX):

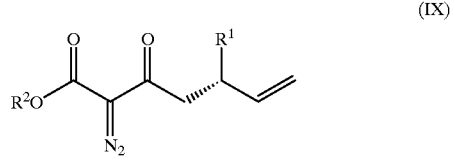

(IX)

with a transition metal catalyst in solvent to form Compound X.

13. The process according to claim 12, wherein the transition metal catalyst comprises a copper catalyst or a rhodium catalyst.

14. The process according to claim 13, wherein the transition metal catalyst comprises a copper catalyst.

15. The process according to claim 14, wherein the copper catalyst is selected from the group consisting of Cu(OTf)$_2$, [(CH$_3$CN)$_4$Cu]PF$_6$, and CuCl+AgOTf.

16. The process according to claim 14, wherein the copper catalyst comprises [L$_p$Cu(I)]Q$^-$ wherein
 wherein each L is a ligand independently selected from $C_2$–$C_6$ olefins, aliphatic $C_2$–$C_6$ nitriles, aliphatic $C_1$–$C_4$ alkyl alcohols, aliphatic $C_2$–$C_6$ ethers and di-ethers, and $C_4$–$C_6$ cyclic ethers and di-ethers;
 p is an integer in the range from 0 to 4; and
 Q$^-$ is a counterion.

17. The process according to claim 16, wherein the copper catayst comprises a catalyst complexed with a chiral ligand.

18. The process according to claim 12, wherein the solvent in step Z3 is selected from the group consisting of $C_3$–$C_{20}$ linear and branched alkanes, $C_1$–$C_{12}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_{10}$ alkyl, $C_4$–$C_8$ dialkoxyalkanes, $C_4$–$C_8$ cyclic ethers and diethers, $C_6$–$C_8$ aromatic ethers, $C_2$–$C_{10}$ dialkyl ketones wherein each alkyl is independently $C_1$–$C_8$ alkyl, $C_1$–$C_6$ alkyl esters of $C_1$–$C_6$ alkylcarboxylic acids, primary $C_1$–$C_{10}$ alkyl alcohols, secondary $C_3$–$C_{10}$ alkyl alcohols, tertiary $C_4$–$C_{10}$ alkyl alcohols, primary amides of $C_1$–$C_6$ alkylcarboxylic acids, N—$C_1$–$C_6$ alkyl secondary amides or N,N-di-$C_1$–$C_6$ alkyl tertiary amides of $C_1$–$C_6$ alkylcarboxylic acids, $C_2$–$C_6$ aliphatic nitriles, and $C_7$–$C_{10}$ aromatic nitriles.

19. The process according to claim 12, wherein the contacting in step Z3 is conducted at a temperature in a range of from about 15 to about 100° C.

20. The process according to claim 12, wherein the catalyst is present in an amount of from about 0.001 to about 30 mole percent based upon the total moles of transition metal and Compound IX.

21. The process according to claim 12, which further comprises (Z2) reacting a beta-ketoester of Formula (VIII):

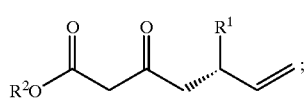
(VIII)

with a hydrocarbyl-sulfonyl azide or a substituted hydrocarbyl-sulfonyl azide in an organic solvent and in the presence of a base to form Compound IX.

22. The process according to claim 21, wherein the sulfonyl azide is of formula $R^3SO_2N_3$;

wherein $R^3$ is $C_1$–$C_4$ alkyl, phenyl, or substituted phenyl, wherein each substituent on the substituted phenyl is independently selected from $C_1$–$C_{18}$ alkyl, $C_1$–$C_{18}$ haloalkyl, halo, cyano, nitro, $C_1$–$C_6$ alkoxy, $C_2$–$C_8$ alkoxyalkyl, $N(R^cR^d)_2$, and $NR^cCOR^d$; wherein each $R^c$ and $R^d$ is independently hydrogen, $C_1$–$C_6$ alkyl, or $(CH_2)_{0-4}CF_3$.

23. The process according to claim 22, wherein the sulfonyl azide is selected from the group consisting of benzenesulfonyl azide, p-toluenesulfonyl azide, dodecyl-benzenesulfonyl azide, and p-acetamidobenzenesulfonyl azide.

24. The process according to claim 21, wherein the azide is present in an amount of at least about 0.5 equivalent per equivalent of Compound VIII.

25. The process according to claim 21, wherein the base in step Z2 is selected from tri-($C_1$–$C_4$ alkyl)amines, N-($C_1$–$C_4$ alkyl)-$C_3$–$C_6$ azacycloalkanes, and N-($C_3$–$C_4$ oxazines).

26. The process according to claim 19, wherein the solvent in step Z2 is selected from $C_1$–$C_6$ linear and branched halogenated alkanes and $C_2$–$C_6$ aliphatic nitriles.

27. The process according to claim 21, wherein the reaction in step Z2 is conducted at a temperature in a range of from about −10 to about 35° C.

28. The process according to claim 21, which further comprises (Z1) reacting a compound of Formula (VI):

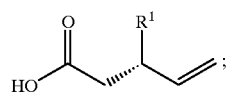
(VI)

with a malonate of Formula (VII):

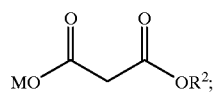
(VII)

in a solvent and in the presence of carbonyldiimidazole, a metal halide, and a base to form Compound VIII; wherein M is an alkali metal.

29. The process according to claim 28, wherein

M is sodium or potassium;

the metal halide is a magnesium halide; and the base is a tri-($C_1$–$C_4$ alkyl)amine.

30. The process according to claim 1, wherein in step Z4 a mixture of Compound 10 of formula:

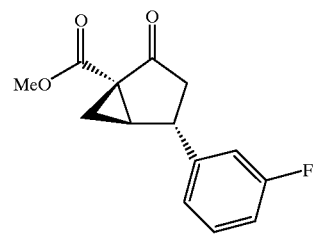
10 and sodium acetate in acetic acid is reacted at a temperature in the range of from about 50 to about 130° C. to open the fused cyclopropyl ring of 10; and in step Z5 the reaction mixture of step Z4 is contacted with an alkali metal hydroxide at a temperature in the range of from about 20 to about 100° C. to form Compound 12 of Formula:

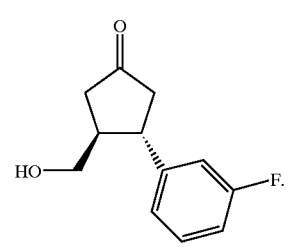
12

31. The process according to claim 30, which further comprises contacting diazo compound 9 of Formula:

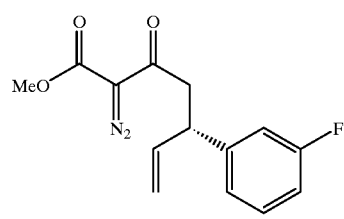
9 with a catalyst selected from [(CH$_3$CN)$_4$Cu]PF$_6$, Cu(OTf)$_2$, and CuCl+AgOTf, in an organic solvent, at a temperature in a range of from about 70 to about 100° C. to form Compound 10.

* * * * *